US011707314B2

(12) United States Patent
To et al.

(10) Patent No.: US 11,707,314 B2
(45) Date of Patent: *Jul. 25, 2023

(54) ABLATION SYSTEM WITH IMPEDANCE NAVIGATION

(71) Applicant: IME Acquisition Sub LLC, Auburndale, MA (US)

(72) Inventors: John To, Newark, CA (US); Paul J. Birkmeyer, Marshfield, MA (US); Samir S. Taneja, Wyckoff, NJ (US); Steffen Jorgensen, Gorlose (DK)

(73) Assignee: IME Acquisition Sub LLC, Auburndale, MA (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/077,841

(22) Filed: Oct. 22, 2020

(65) Prior Publication Data

US 2021/0275243 A1 Sep. 9, 2021

Related U.S. Application Data

(63) Continuation of application No. 16/855,429, filed on Apr. 22, 2020, now Pat. No. 10,864,036, which is a
(Continued)

(51) Int. Cl.
*A61B 18/14* (2006.01)
*A61B 18/00* (2006.01)
*A61B 34/30* (2016.01)

(52) U.S. Cl.
CPC .............. *A61B 18/14* (2013.01); *A61B 34/30* (2016.02); *A61B 2018/00029* (2013.01);
(Continued)

(58) Field of Classification Search
CPC ................... A61B 18/14; A61B 34/30; A61B 2018/00029; A61B 2018/00547;
(Continued)

(56) References Cited

U.S. PATENT DOCUMENTS 4,699,157 A 10/1987 Shonk
5,507,743 A 4/1996 Edwards et al.
(Continued)

FOREIGN PATENT DOCUMENTS

DE 19713797 10/1997
EP 2475323 7/2012
(Continued)

OTHER PUBLICATIONS

Written opinion and search report for PCT/US2020/31947, To, et al.—owned by Applicant, dated May 10, 2019.
(Continued)

*Primary Examiner* — Adam Z Minchella
(74) *Attorney, Agent, or Firm* — Foley & Lardner LLP

(57) ABSTRACT

Dual coil ablation systems are provided. Methods of using the systems to ablate tissue are also provided. The dual coil ablation systems can include a first guide needle and a second guide needle, and the methods can include securing the tissue and guiding the dual coil ablation system into the tissue for the ablation, the securing and the guiding facilitated by the first guide needle and the second guide needle. The dual coil ablation systems can also include a phase-offset between the coils to achieve a significant and surprising enhancement to the energy density provided by the systems, and the uniformity of ablation provided by the methods.

20 Claims, 13 Drawing Sheets

Related U.S. Application Data continuation of application No. 16/409,668, filed on May 10, 2019, now Pat. No. 10,667,855.

(52) U.S. Cl.
CPC ............... *A61B 2018/00547* (2013.01); *A61B 2018/00577* (2013.01); *A61B 2018/00875* (2013.01); *A61B 2018/1435* (2013.01); *A61B 2018/1475* (2013.01)

(58) Field of Classification Search
CPC ........... A61B 2018/00577; A61B 2018/00875; A61B 2018/1435; A61B 2018/1475
See application file for complete search history.

(56) References Cited

U.S. PATENT DOCUMENTS

| | | |
|---|---|---|
| 5,676,662 A | 10/1997 | Fleischhacker et al. |
| 5,688,267 A | 11/1997 | Panescu |
| 5,837,006 A | 11/1998 | Ocel et al. |
| 5,873,877 A | 2/1999 | McGaffigan et al. |
| 5,921,982 A | 7/1999 | Lesh et al. |
| 5,928,229 A | 7/1999 | Gough et al. |
| 5,957,935 A | 9/1999 | Brown et al. |
| 6,086,583 A | 7/2000 | Ouchi |
| 6,165,170 A | 12/2000 | Wynne et al. |
| 6,167,292 A | 12/2000 | Badano et al. |
| 6,258,087 B1 | 7/2001 | Edwards et al. |
| 6,385,472 B1 | 5/2002 | Hall et al. |
| 6,398,711 B1 | 6/2002 | Green et al. |
| 6,415,679 B1 | 7/2002 | Chiodo |
| 6,464,697 B1 | 10/2002 | Edwards et al. |
| 6,497,704 B2 | 12/2002 | Ein-Gal |
| 6,544,176 B2 | 4/2003 | Mikus et al. |
| 6,638,275 B1 | 10/2003 | McGaffigan et al. |
| 6,641,580 B1 | 11/2003 | Sharkey et al. |
| 6,911,019 B2 | 6/2005 | Mulier et al. |
| 6,923,807 B2 | 8/2005 | Ryan et al. |
| 6,939,348 B2 | 9/2005 | Malecki et al. |
| 6,974,455 B2 | 12/2005 | Garabedian et al. |
| 7,171,255 B2 | 1/2007 | Holupka et al. |
| 7,309,325 B2 | 12/2007 | Mulier et al. |
| 7,680,543 B2 | 3/2010 | Azure |
| 7,794,459 B2 | 9/2010 | Faure |
| 7,831,293 B2 | 11/2010 | Ellis et al. |
| 7,879,030 B2 | 2/2011 | Paul et al. |
| 8,317,785 B2 | 11/2012 | Faure |
| 9,114,252 B2 | 8/2015 | Yu et al. |
| 9,220,892 B2 | 12/2015 | Faure et al. |
| 9,445,866 B2 | 9/2016 | Faure et al. |
| 9,655,676 B2 | 5/2017 | Faure et al. |
| 9,895,190 B2 | 2/2018 | Trieu |
| 9,901,396 B2 | 2/2018 | Faure et al. |
| 10,398,526 B2 | 9/2019 | Faure et al. |
| 10,667,855 B1 | 6/2020 | To et al. |
| 10,864,036 B2 | 12/2020 | To et al. |
| 2002/0156361 A1 | 6/2002 | Popowski et al. |
| 2004/0122422 A1* | 6/2004 | Ein-Gal ............. A61B 17/3478 604/20 |
| 2005/0085807 A1 | 4/2005 | Venturelli |
| 2007/0179494 A1* | 8/2007 | Faure ................. A61B 18/1477 606/41 |
| 2008/0249525 A1 | 5/2008 | Lee et al. |
| 2009/0030339 A1 | 1/2009 | Cheng et al. |
| 2011/0071380 A1 | 3/2011 | Goldenberg et al. |
| 2011/0288541 A1* | 11/2011 | Faure ................. A61B 18/1482 606/33 |
| 2017/0151033 A1* | 6/2017 | Faure .................... A61B 90/11 |
| 2019/0336237 A1 | 11/2019 | Faure et al. |

FOREIGN PATENT DOCUMENTS

| | | |
|---|---|---|
| WO | WO 2000/35531 | 6/2000 |
| WO | PCT/BE2004/000073 | 11/2004 |
| WO | PCT/IB2005/001774 | 1/2006 |
| WO | WO 2007/064937 | 6/2007 |
| WO | WO 2007/085953 | 8/2007 |
| WO | WO 2007/144004 | 12/2007 |
| WO | PCT/EP2009/055984 | 11/2009 |
| WO | PCT/EP2016/079291 | 6/2017 |
| WO | PCT/US202031947 | 5/2019 |

OTHER PUBLICATIONS

European search report for 04733277, dated Oct. 7, 2005, Andre Faure—owned by Applicant.
European search report for 05758887, dated Apr. 4, 2007, Trod Medical—owned by Applicant.
European search report for 09745842, dated May 18, 2011, Faure, et al.—owned by Applicant.
Written opinion and search report for PCT/BE2004/000073, dated Nov. 25, 2004, Andre Faure—owned by Applicant.
Written opinion and search report for PCT/IB2005/001774, dated Jan. 5, 2006, Trod Medical—owned by Applicant.
Written opinion and search report for PCT/EP2009/055984, dated Nov. 19, 2009, Faure, et al.—owned by Applicant.
Written opinion and search report for PCT/EP2016/079291, dated Jun. 8, 2017, Faure, et al.—owned by Applicant.

* cited by examiner

ABLATION SYSTEM WITH IMPEDANCE NAVIGATION

CROSS-REFERENCE TO RELATED APPLICATIONS

This application is a continuation of U.S. patent application Ser. No. 16/855,429, filed Apr. 22, 2020, which is a continuation of U.S. application Ser. No. 16/409,668, filed May 10, 2019, now U.S. Pat. No. 10,667,855, issued Jun. 2, 2020, each of which is hereby incorporated herein by reference in it's entirety.

BACKGROUND

Field of the Invention

The teachings are directed, generally, to dual coil ablation systems, and methods of using the systems to ablate tissue.

Description of the Related Art

Bipolar RF energy is an effective way to locally and accurately destroy diseased tissue such as tumors and polyps, as an electrical current density for heating tissue to destruction is focally concentrated between the electrodes of opposite polarity. State-of-the-art systems can include an electrode in the shape of a helical coil, for example, to encase a target tissue and thus confine the current flow for focal tissue heating. The helical coil electrode forms a large three dimensional structure to heat and ablate a large volume of tissue within that structure, providing there is a separate electrode inside the coil.

Such ablation systems can include both single coil and dual coil electrodes, each of which has added great value in the art of ablation technologies. Such systems can include, for example, a straight needle electrode that is directed into the tissue to be ablated. The straight needle electrode targets the tissue for positioning a coil electrode. The straight needle electrode is then removed, and the coil electrode is directed into the tissue. The straight needle is again directed into the tissue to have the two electrodes in the tissue for the ablation.

Locating and Securing Target Tissue for Ablation

Although placement of the straight needle electrode identifies the location of the tissue to be ablated, removal of the straight needle electrode from the tissue prior to placement of the coil electrode allows for greater movement of the tissue, and the coil electrode can deflect during placement. This is because a coil electrode is flexible, causing it to veer off laterally as it is advanced into the tissue and, potentially, missing the intended target tissue. This requires extra time and effort from the user of the systems herein to position the coil.

Moreover, the problem of locating tissue and securing it's location is often exacerbated by the target tissue being different than surrounding tissue, for example, stiffer or softer. For example, the prostate capsule is tougher and stiffer than surround tissue matrix. Also, the tissue within the prostate is non-homogenous. When trying to introduce any needle into the capsule, whether helical or straight, the capsule tissue is expected to deflect away from the needle tip, or rotate from torsion, for example. Clearly, this difference between the target tissue and surrounding tissue adds variability to the methods, requiring the user of the systems herein to spend additional time in the procedure.

Enemy Density Distribution

The use of a straight electrode with a coil electrode also presents energy density problems. The coil electrode has a larger surface area due to the much longer path for current to travel from the proximal end of the coil electrode to the distal end of the coil electrode. The straight needle electrode, comparatively, is expected to have a much higher current density, as it has less surface area due to the smaller distance traveled by the current from the proximal end of the straight needle electrode to the distal end of the straight needle electrode. As such, the tissue near the straight needle electrode heats quite fast relative to the tissue near the outer coil electrode, and this adversely affects the ablation achieved in the ablation system. If an inner coil is used instead of straight needle electrode, for example, you get significantly better heating and, thus, improved ablation of the tissue.

Some systems can include two coil electrodes, for example, which are directed into the tissue after the location of the tissue is targeted. Since coil electrodes deflect and there are two of them, the problem of deflection can be doubled in the dual coil electrode systems. Each of the coils in a dual coil system can separately veer off course, either contacting each other and causing a short, or a current density distribution that is less uniform. As such, the tissue can heat up too quickly and burn where the electrodes are too close, for example, or heat up too slowly or inadequately where the electrodes are too far apart, perhaps not enough to kill the diseased cells.

Likewise, the use of a dual coil electrode ablation system can also present energy density problems due to the variability and non-selectivity of the alignment of the dual helical coils relative to one another. The dual coil systems can have an outer coil electrode and an inner coil electrode, the outer coil electrode having a greater conductive path due to the much longer distance traveled, and much greater amount of material traversed, from the proximal end of the coil electrode to the distal end of the coil electrode, and thus has greater surface area. The straight needle electrode, comparatively, is expected to have a much higher current density, due to the smaller distance traveled, and much less amount of material traversed, by the current from the proximal end of the straight needle electrode to the distal end of the straight needle electrode. As such, the tissue near the straight needle electrode is expected to heat quite fast relative to outer coil electrode, and so this configuration is, likewise, expected to adversely affect the ablation achieved. If an inner coil is used instead of straight needle electrode to configure a dual coil ablation system, for example, you can achieve significantly better heating and, thus, an improved ablation of the tissue.

Likewise, the coils in a dual coil electrode ablation system can flex and come in very close proximity to, or even contact, one another, resulting in shorting of the system and/or production of high levels of localized heating relative to other regions of the tissue to be ablated.

The systems and methods provided herein will be appreciated by those of skill in the art of ablation, as the systems and methods surprisingly enhance the quality of ablation technologies by at least, (i) improving the accuracy of the placement of the electrodes into the tissue by securing the tissue to be ablated with a plurality of guide needles; (ii) improving the accuracy of the placement of the electrodes into the tissue by guiding the placement of the electrodes with the plurality of guide needles; (iii) improving the versatility of the system by allowing a user to select sizes and shapes of regions to be ablated through the use of a multi-pattern guide template; and (iv) improving the energy density distribution through the use of a phase-offset configuration between the coil electrodes. One of skill will appreciate that these improved systems and methods can include one or more impedance feedback components to tell the user of the device the type of tissue in which the electrodes are located, and the extent of ablation achieved. All of these improvements add significant value to the field of ablation technologies, making it more effective in terms of achieving the desired ablation for the targeted area, easier, more cost-effective, and less risky for the user of the systems herein to perform ablation procedures.

SUMMARY

Dual coil ablation systems and methods of using the systems to ablate tissue are provided. In some embodiments, the dual coil ablation systems can include a first guide needle and a second guide needle, and the methods can surprisingly improve the accuracy of the placement of the electrodes through, for example, an improved securing of the tissue to be ablated, and a guiding of each coil in the dual coil ablation system into the tissue for the ablation. The securing and the guiding is facilitated by the first guide needle and the second guide needle. In some embodiments, the dual coil ablation systems can include a phase-offset between the coils to achieve a significant and surprising enhancement to the energy density provided by the systems and, as a result, a significant and surprising enhancement to the uniformity of ablation achieved.

In some embodiments, a guided, dual coil ablation system is provided. The system can have an outer coil electrode having an inner diameter ranging from about 4 mm to about 40 mm, or about 4 mm to about 10 mm, for example, and a lumen having a luminal surface forming the inner diameter, an outer length, and an outer coil axis. In some embodiments, the tissue to be ablated is prostate tissue, and the outer diameter of the outer coil ranges from about 10 mm to about 16 mm.

In some embodiments, it can also have an inner coil electrode having an outer diameter that ranges from about 2 mm to about 39 mm and is at least 1.0 mm smaller than the inner diameter of the outer coil electrode, an outer surface, an inner length, and an inner coil axis. And, in many embodiments, the system has a plurality of guide needles including a first guide needle having a first guide axis and a first guide length; and, a second guide needle having a second guide axis and a second guide length. The systems can also include a hub having a first ablation template, the first ablation template including a first outer electrode port adapted for receiving the outer coil electrode, a first inner electrode port adapted for receiving the inner coil electrode, a first guide port for receiving the first guide needle, and a second guide port for receiving the second guide needle.

The first ablation template can be configured for positioning the first guide needle relative to the second guide needle in or around a tissue to be ablated, the positioning including using the first guide port and the second guide port to align the first guide axis with the second guide axis in an at least substantially parallel arrangement; and, creating an annular ablation region around the first guide needle and the second guide needle in the tissue to be ablated upon assembly of the system, the inner coil electrode aligned at least substantially concentric with the outer coil electrode; the annular ablation region configured to be (i) bordered by the outer surface of the inner coil electrode and the luminal surface of the outer coil electrode and (ii) having a thickness ranging from about 0.5 mm to about 10 mm. In some embodiments, the system is configured to serve as a "guided, dual coil ablation system" that secures the tissue while guiding placement of the dual coils for the ablation.

To further improve the systems, in some embodiments, the systems can include a plurality of guide needles that further include a third guide needle having a third guide axis and a third guide length. The annular ablation region can also be around the third guide needle with the third guide axis in an at least substantially parallel arrangement with the first guide axis with the second guide axis. Moreover, the first ablation template can be configured to further include a third guide port for receiving the third guide needle.

The devices are even further improved in that they can be configured for an improved energy density profile to improve ablation. As such, in some embodiments, the outer coil has an outer pitch, the inner coil has an inner pitch, and the outer pitch is positioned to have a phase-offset with respect to the inner pitch, the phase-offset ranging from between 30° to 180°.

The devices are even further improved in that they can be configured to have an outer coil electrode handle in an operable connection with the outer coil electrode and configured for adjusting the depth of the outer coil electrode in the tissue; and, an inner coil electrode handle in an operable connection with the inner coil electrode and configured for adjusting the depth of the inner coil electrode in the tissue.

The devices are even further improved in that the inner electrode can be configured as an inner coil with a lumen. In some embodiments, however, the inner electrode can have a solid core, and no lumen. For example, the solid core can have a spiral conductor wrapping around the solid core, such that it operates similar to an inner coil electrode. Likewise, in some embodiments, the inner electrode can be straight shaft. In some embodiments, the inner electrode can be a straight shaft with a spiral conductor wrapping around the straight shaft, so that it operates like an inner coil electrode. In some embodiments, the spiral conductor is a spiral protrusion. Such an inner coil, for example, can provide a small diameter with sufficient strength to penetrate a target tissue without undue deformation, and sufficient conductivity to provide the ablation. the outer diameter of the inner coil can be about 2 mm, about 3 mm, about 4 mm, about 5 mm, about 6 mm, about 7 mm, about 8 mm, about 9 mm, about 10 mm, or any range therein in increments of 1 mm.

In some embodiments, the inner electrode can be a non-conducting material, such as an insulator material. Moreover, in some embodiments, the inner electrode can be radiolucent, or at least substantially radiolucent. Likewise, in some embodiments, the inner electrode can be echogenic, or at least substantially echogenic.

The systems can be even further improved through the addition of self-tapping tips on the guide needles, for example, in order to ease penetration of target tissue by a user of the system. The systems can be even further improved through the addition of self-centering tips on the guide needles, for example, in order to ease maintaining the intended direction of penetration of target tissue by a user of the system. As such, in some embodiments, the plurality of guide needles can include a needle having a self-tapping tip, or a self-centering tip.

The systems can be even further improved by facilitating a pattern of ablations that can expand the amount and/or shapes used to ablate the tissue. In some embodiments, for example, the hub is a multi-pattern guide template further comprising n additional ablation templates, where n is the number of ablation on the hub, n ranging from 1 to 10. One of skill will appreciate that the plurality of the ablation templates can be used to create a plurality of ablation patterns to ablate the tissue.

Likewise, the systems and methods provided herein can include feedback to the user to enhance and/or ease the user's experience in the ablation of tissue, as well as reduce the risk and time involved in performing the procedures. For example, in some embodiments, the systems can further comprise one or more impedance electrodes operable to provide a feedback response for navigating the penetration of the ablation device into the target tissue, the navigating including monitoring the electrical impedance of a tissue as the ablation device penetrates the tissue.

Methods of using the devices are also provided. In some embodiments, the methods include a method of ablating tissue that includes obtaining any of the ablation systems taught herein which can include, for example, an ablation system having an inner coil electrode with an outer surface and an inner pitch, an outer coil electrode with an inner surface and an outer pitch, a first guide needle with a first guide axis, a second guide needle with a second guide axis. As noted, the systems can also include a hub having a first ablation template with a first outer electrode port adapted for receiving the outer coil electrode, a first inner electrode port adapted for receiving the inner coil electrode, a first guide port for receiving the first guide needle, and a second guide port for receiving the second guide needle. An additional step will include locating a tissue for ablation, also referred to as a "target tissue". Another step includes aligning the first ablation template over the tissue. Another step includes receiving the first guide needle in the first guide port of the first ablation template. The first guide needle is inserted into the target tissue. The methods can include receiving the second guide needle in the second guide port of the first ablation template. And, of course, the method can include inserting the second guide needle into the target tissue.

Due to the presence of the inner coil and the outer coil, in some embodiments, the methods include creating an annular ablation region in the tissue to be ablated. The creating can include receiving the inner coil electrode in the first inner electrode port of the first ablation template; receiving the outer coil electrode in the first outer electrode port of the first ablation template; and, inserting the outer coil electrode into the tissue. In some embodiments, the inserting can include slidably translating the luminal surface of outer coil electrode around the first guide needle and the second guide needle, wherein the outer coil electrode contains the first guide needle and the second guide needle.

Likewise, in some embodiments, the methods include inserting the inner coil electrode into the tissue. As such, in these embodiments, the inserting can include slidably translating the outer surface of inner coil electrode concentric, or at least substantially concentric with the outer coil electrode to create the annular ablation region. One of skill will appreciate that, given the above steps, the first guide needle and the second guide needle can be in the annular ablation region.

The methods can include removing the first guide needle and the second guide needle from the target tissue; and, ablating the tissue. One of skill will appreciate that the methods provided herein can include securing the tissue and guiding the dual coil ablation system into the target tissue for the ablation, the securing and the guiding facilitated by the first guide needle and the second guide needle.

The prostate gland of a male subject is a common tissue that can be subject to an ablation in the treatment of the subject. In some embodiments, the condition is a benign prostatic hypertrophy (BPH), for example. As such, the methods can include ablating a prostate tissue of a subject and include obtaining the ablation devices and systems taught herein, and locating the prostate tissue for ablation, and aligning the first ablation template over the prostate tissue to be ablated. In some embodiments, the method can include receiving the first guide needle in the first guide port of the first ablation template; inserting the first guide needle into the prostate tissue. In some embodiments, the methods can include receiving the second guide needle in the second guide port of the first ablation template; and, inserting the second guide needle into the prostate tissue.

Likewise, since any of the ablation systems taught herein can be used, the methods also further include the use of a third guide needle having a third guide axis; and, use of the first ablation template further includes use of a third guide port for receiving the third guide needle. As such, the methods can include inserting the third guide needle into the tissue; and, receiving the third guide needle in the third guide port of the first ablation template. It should be appreciated, given the teachings provided herein, that the inserting of the outer coil electrode into the tissue can include slidably translating the luminal surface of outer coil electrode over the first guide needle, the second guide needle, and the third guide needle. One of skill will further appreciate that the first guide needle, the second guide needle, and the third guide needle can be in the annular ablation region. And, as such, the removing can include removing the first guide needle, the second guide needle, and the third guide needle from the tissue, in some embodiments.

Moreover, the phase-offset feature can be used to significantly improve the methods taught herein. In some embodiments, the methods can include establishing a phase-offset between the outer pitch of the outer coil electrode and the inner pitch of the inner coil electrode, the phase-offset ranging from between 30° to 180°. As such, it will be appreciated that a significantly improved ablation of the target tissue can occur within the annular ablation region formed having the phase offset between the outer coil electrode and the inner coil electrode.

The handle assemblies provided in the systems can be quite useful in improving the ease of the ablation procedure. As such, in some embodiments, the methods can include adjusting the depth of the outer coil electrode with an outer coil electrode handle in an operable connection with the outer coil electrode; and, adjusting the depth of the inner coil electrode with an inner coil electrode handle in an operable connection with the inner coil electrode.

As discussed herein, the systems can include a hub with a multi-pattern guide template having n additional ablation templates to form a desired scope or shape of ablation, where n is the number of ablation templates and ranges from 1 to 10. As such, in some embodiments, the methods include creating an ablation pattern to ablate the tissue with a plurality of ablation templates; and, ablating the tissue with the ablation pattern.

One of skill will appreciate that any one or any combination of the above features can be combined into the devices, systems, and methods taught herein and, accordingly, the above summary includes any one, or any combination of, such features in the technology provided herein.

DETAILED DESCRIPTION OF THE INVENTION

Dual coil ablation systems are provided. Methods of using the systems to ablate tissue are also provided. The dual coil ablation systems can include a first guide needle and a second guide needle, and the methods can include securing the tissue and guiding the dual coil ablation system into the tissue for the ablation, the securing and the guiding facilitated by the first guide needle and the second guide needle. The dual coil ablation systems can also include a phase-offset between the coils to achieve a significant and surprising enhancement to the energy density provided by the systems, and the uniformity of ablation provided by the methods. One of skill will appreciate the improvements set-forth herein, and particularly as they provide improved systems and procedures for ablating animal tissue in the treatment of a subject.

The term "animal" can be used interchangeably, in some embodiments, with the terms "subject" and "patient". Such terms can be used to refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like. Moreover, "tissue" can be used to refer, for example, to epithelial tissue, connective tissue, muscle tissue and/or nerve tissue, in some embodiments. One of skill will appreciate that epithelial tissues form the surface of the skin, and line many cavities of the body and covers the internal organs; connective tissue includes cartilage, bone, adipose, and blood. Muscle tissue includes skeletal, smooth, and cardiac muscle; and the neural tissues include neurons that process and transfer information throughout a subject's body. In some embodiments, any tissue that is desirable to remove, including cancerous tissue, can be removed using the ablation systems, devices, and methods provided herein.

Guide Needles Provide Stability

Figure 1:
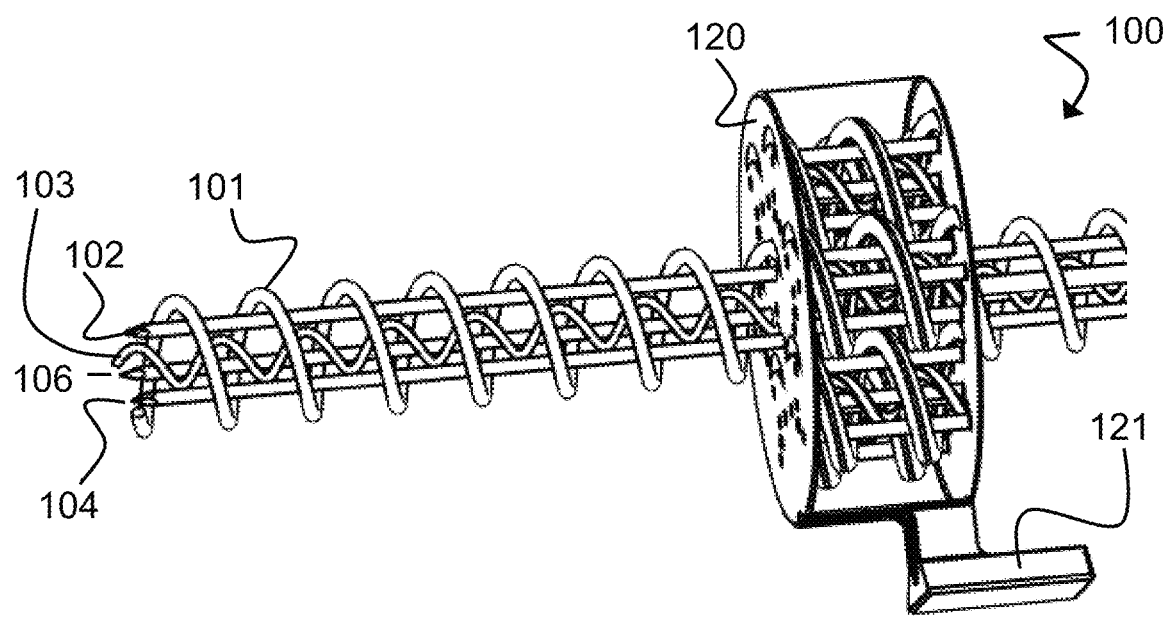
FIG. 1 is perspective view of an ablation device, according to some embodiments.

In some embodiments, a guided, dual coil ablation system is provided, and the systems can have an inner ablation electrode and an outer ablation electrode. The inner ablation electrode can be a coil, and the outer ablation electrode can be a coil. FIG. 1 is perspective view of an ablation device, according to some embodiments. As shown in FIG. 1, the dual coil ablation systems 100 can only include a first guide needle 102 and a second guide needle 104, in some embodiments. It is acknowledged that a third guide needle 106 is shown in FIG. 1, but it is not needed in some embodiments. The methods of using these devices, as provided herein, can surprisingly improve the accuracy of the placement of electrodes by, for example, at least improving the securing of the tissue to be ablated, and guiding each coil in the dual coil ablation system into the tissue for the ablation. After reading the teachings provided herein, one of skill will appreciate the value of at least the steps of the securing and the guiding of the electrodes, each of which can be facilitated by at least the first guide needle 102 and the second guide needle 104 and, in some embodiments, additional guide needles, including the third guide needle 106. Those of skill will appreciate that the guide needles can help to avoid undesirable situations in which the inner ablation electrode and the outer ablation electrode either come too close together due to bending, or even make contact, causing a short, either situation of which can cause the ablated tissue to over-necrose. Additionally, if the inner ablation electrode is close to the outer ablation electrode, tissue on the opposite side of the inner electrode may be correspondingly under-ablated, or will not achieve necrosis, potentially not achieving cell death inside the target area of the distal part of the outer coil.

The system can have an outer coil electrode 101 having an inner diameter ranging from about 4 mm to about 20 mm, a lumen having a luminal surface forming the inner diameter, an outer length, and an outer coil axis. In some embodiments, it can also have an inner coil electrode 103 having an outer diameter that ranges from about 2 mm to about 19 mm and is at least 1.0 mm smaller than the inner diameter of the outer coil electrode, an outer surface, an inner length, and an inner coil axis. And, in many embodiments, the system has a plurality of guide needles including a first guide needle 102 having a first guide axis and a first guide length; and, a second guide needle 104 having a second guide axis and a second guide length.

In some embodiments, the system can have an outer coil electrode having an inner diameter ranging from about 4 mm to about 40 mm, or about 4 mm to about 10 mm, for example, and a lumen having a luminal surface forming the inner diameter, an outer length, and an outer coil axis. As such, in some embodiments, the inner diameter of the outer coil, and the outer diameter of the outer coil can be about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 30 mm, about 31 mm, about 32 mm, about 33 mm, about 34 mm, about 35 mm, about 36 mm, about 37 mm, about 38 mm, about 39 mm, about 40 mm, or any range therein in increments of 1 mm. And, the inner diameter of the inner coil, and the outer diameter of the inner coil can be about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, or any range therein in increments of 1 mm. In some embodiments, the tissue to be ablated is prostate tissue, and the outer diameter of the outer coil ranges from about 10 mm to about 40 mm, about 10 mm to about 30 mm, about 10 mm to about 20 mm, or about 10 mm to about 16 mm. However, in some embodiments, the outer diameter of the outer coil electrode can range from about 4 mm to about 90 mm, about 4 mm to about 80 mm, about 4 mm to about 70 mm, about 4 mm to about 60 mm, about 4 mm to about 50 mm, about 4 mm to about 40 mm, or any range therein in increments of 1 mm.

In some embodiments, it can also have an inner coil electrode having an outer diameter that ranges from about 2 mm to about 39 mm, about 2 mm to about 29 mm, about 2 mm to about 19 mm, or about 2 mm to about 9 mm and is at least 1.0 mm smaller than the inner diameter of the outer coil electrode, an outer surface, an inner length, and an inner coil axis. And, in many embodiments, the system has a plurality of guide needles including a first guide needle having a first guide axis and a first guide length; and, a second guide needle having a second guide axis and a second guide length. The systems can also include a hub having a first ablation template, the first ablation template including a first outer electrode port adapted for receiving the outer coil electrode, a first inner electrode port adapted for receiving the inner coil electrode, a first guide port for receiving the first guide needle, and a second guide port for receiving the second guide needle.

Figure 2:
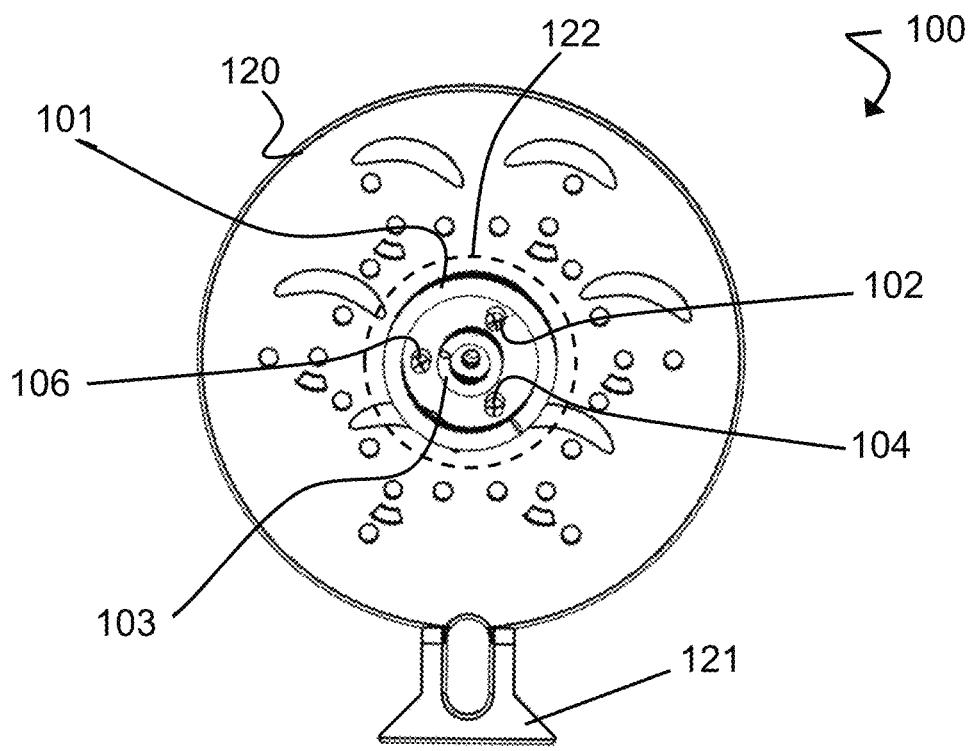
FIG. 2 is plan view of an ablation device from the end having the dual coils, according to some embodiments.

FIG. 2 is plan view of an ablation device from the end having the dual coils and a hub, according to some embodiments. As shown in FIG. 2, the systems can also include a hub 120 having a first ablation template 122. In some embodiments, the hub can be made of a plastic, for example, perhaps an ABS, nylon, polyethylene, acetal, fluoropolymer, or polyurethane. In some embodiments, the hub can be made of any material suitable for 3D printing such as SOMOS® WATERSHED or PERFORM. In some embodiments, the hub can be made from a metal, for example, a steel alloy such as stainless steel, a titanium alloy, or a cobalt alloy such as cobalt chromium. The hub can be fabricated using 3D printing, for example, SLA, SLS, fused deposition, or DMLS, or machined in separate pieces and joined together, or molded. The template can be coated with fluoropolymer or parylene for plastic and it can be anodized or coated with fluoropolymer or parylene for metal for passivity and lubricity. The choice of manufacturing materials should include those that are sterilizable, in some embodiments. The devices need to be at least sterilized for a single use, and perhaps repeatedly sterilized. Sterilization can include the use of ethylene oxide, hydrogen peroxide, radiation such as electron irradiation, or steam sterilization.

Ancillary positioning devices can be configured for attachment to the ablation devices taught herein. In some embodiments, the mount/handle 121 is releasably attached to a mechanical device. In some embodiments, the mechanical device comprises a positioning table (not shown), which can translate linearly, in an X-Y direction, in an X-Y-Z direction, or in any position or vector in space around the tissue to be ablated. In some embodiments, the mechanical device comprises a robotic arm. Regardless of the configuration and control of the mechanical device, the mechanical device is configured for orienting the position of the ablation device relative to the tissue of a subject.

The first ablation template can be configured for positioning the first guide needle relative to the second guide needle in or around a tissue to be ablated, the positioning including using the first guide port and the second guide port to align the first guide axis with the second guide axis in an at least substantially parallel arrangement; and, creating an annular ablation region around the first guide needle and the second guide needle in the tissue to be ablated upon assembly of the system, the inner coil electrode aligned at least substantially concentric with the outer coil electrode; the annular ablation region configured to be (i) bordered by the outer surface of the inner coil electrode and the luminal surface of the outer coil electrode and (ii) having a thickness ranging from about 0.5 mm to about 10 mm. In some embodiments, the system is configured to serve as a "guided, dual coil ablation system" that secures the tissue while guiding placement of the dual coils for the ablation.

To further improve the systems, in some embodiments, the systems can include a plurality of guide needles that further include a third guide needle having a third guide axis and a third guide length. The annular ablation region can also be around the third guide needle with the third guide axis in an at least substantially parallel arrangement with the first guide axis with the second guide axis. Moreover, the first ablation template can be configured to further include a third guide port for receiving the third guide needle.

In some embodiments, the guide needles can circumscribe the inner diameter of the outer ablation coil. For example, in some embodiments, a guide needles can be located from about 0 mm to about 5 mm inwards from the luminal surface of the outer ablation coil. In some embodiments, a guide needle can be located from about 0.5 mm to about 2 mm inwards from the luminal surface of the outer ablation coil. In fact, one of skill will appreciate that the guide needles can be placed at the outer margins of the target tissue to be ablated, either within the outer margins of the target tissue, in some embodiments, or surrounding the outer margins of the target tissue. The coil can then be screwed in to encase the target tissue by rotating the coil relative to the guide and tissue.

One of skill will appreciate that the outer ablation coil and the inner ablation coil can be designed for ease of insertion in to the target tissue. For example, the tip of the outer ablation coil and/or inner ablation coil can have a bevel, the outer ablation coil having the bevel on the luminal surface of the coil, and the inner ablation coil having the bevel on the outer surface of the coil, to facilitate a "ramping-away-from", or inner deflection from, each of the guide needles, should the coil come into contact with a guide needle in passing as it is screwed in.

In some embodiments, guide needles can be curved, but follow parallel paths with respect to each other and be positioned evenly distributed in the annular ablation region such that one or both coils can follow a curved path towards the target tissue.

In some embodiments, components of the ablation device, such as the guide needles, and/or electrodes, can be manufactured, having materials that are independently selected or shared, using a non-conductive material to prevent a "short" between outer and inner electrode. In some embodiments, the guide needles can be made entirely from a non-conductive material, and the electrodes can be made of a conductive material. In some embodiments, the guide needles can comprise a metal selected from the group consisting of steel alloys such as stainless steel, a titanium alloy, a cobalt alloy like cobalt chromium, and combinations thereof. In some embodiments, the guide needles can be coated with polymer such as, for example, a fluoropolymer which can include, for example, PTFE, ETFE, or PVDF, PEEK, silicone, or polyimide, or a ceramic material which can include, for example, alumina or zirconia. One of skill will appreciate that, in some embodiments, a ceramic sleeve can be applied on metal core to stiffen the wire to reduce flexing as it traverses a tissue. Moreover, in some embodiments, an electrically insulative sleeve can be made to slide over the electrode, so that depth of ablation can be varied quickly and easily by adjusting the position of the sleeve relative to the electrode, rather than the electrode, varying depth of ablation without moving the electrode.

Guide needles can have any of several designs considered to be functional and desired to those of skill. For example, the distal section of the guide needle can be smaller than the proximal section for less resistance during an insertion into a tough tissue, near or at the target tissue, such as prostate capsule. This distal thin section can range from, for example, about 0.1" to about 2" in length, in some embodiments, or from about 0.5" to about 1" in length, in some embodiments. The distal section can be made of a smaller diameter, as it does not experience as much bending force as the proximal section. In some embodiments, the guide needle can be an assembly of a metal wire at the center and a ceramic sleeve on the proximal section. In some embodiments, the outer diameter of the core wire can range from about 0.25" to about 0.75". The entire wire, or perhaps just part of the wire, perhaps the tip of the wire, can be coated with polymer or ceramic for electrical insulation. One of skill will appreciate temperature feedback, in some embodiments, so a thermocouple can be embedded in the distal section of the wire to monitor tissue temperature or provide temperature feedback to the user of the device. In fact, in some embodiments, the guide needle can be hollow to allow coolant fluid to drip into the tissue during ablation. In some embodiments, the hollow guide needle can have a thermocouple wire placed inside, and at the desired depth. And, in some embodiments, one of skill will appreciate a conductive wire, so in some embodiments the guide needle can be conductive in the distal section which, for example, allows the guide need to act as an electrode.

In some embodiments, the guide needles can be inserted into the target tissue independently. In some embodiments the guide needles can be inserted into the target tissue together. For example, the guide needles can be an assembly that is inserted as a unit. In some embodiments, the assembly may be joined to a handle as unit to be inserted together. Or, in another example, they can be separate and inserted independently into the body of the patient. A handle, for example, can be configured with a position pin to fix the axial position of the guide needle relative to the hub. The position pin can slide relative to the handle and be locked against the hub surface.

Moreover, the guide needles provide better targeting through improved imaging during the ablation process. For example, it's easier see guide needles with ultrasound during their shape and placement, when compared to the movement of the helical coil electrodes. This provides an improved accuracy of the placement of guide needles and, thus, the electrodes that they guide. Likewise, this improved accuracy facilitates use of the guide template, the combination of imaging of the guide needles and template placement optimizing the overlap of the inner coil electrode and the outer coil electrode, and securing the target tissue, while placing the guide needles, and then the inner coil electrode and the outer coil electrode in an adjacent location.

Control Handle Assemblies

The devices are even further improved in that they can be configured to have an outer coil electrode handle in an operable connection with the outer coil electrode and configured for adjusting the depth of the outer coil electrode in the tissue; and, an inner coil electrode handle in an operable connection with the inner coil electrode and configured for adjusting the depth of the inner coil electrode in the tissue. The handle assemblies provided in the systems can be quite useful in improving the ease of the ablation procedure. As such, in some embodiments, the methods can include adjusting the depth of the outer coil electrode with an outer coil electrode handle in an operable connection with the outer coil electrode; and, adjusting the depth of the inner coil electrode with an inner coil electrode handle in an operable connection with the inner coil electrode.

Figure 3:
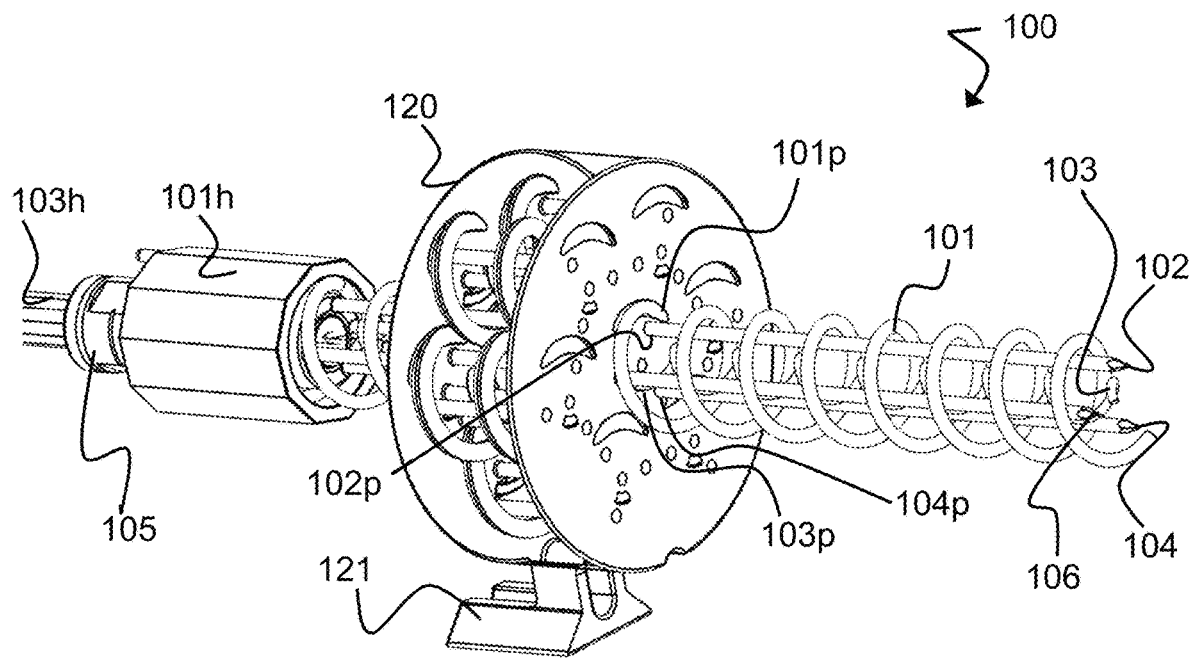
FIG. 3 is perspective view of an ablation device with a control handle assembly, according to some embodiments.

FIG. 3 is perspective view of an ablation device with a control handle assembly, according to some embodiments. As shown in FIG. 3, the first ablation template can include a first outer electrode port 101$p$ adapted for receiving the outer coil electrode 101, a first inner electrode port 103$p$ adapted for receiving the inner coil electrode 103, a first guide port 102$p$ for receiving the first guide needle 102, and a second guide port 104$p$ for receiving the second guide needle 104. In some embodiments, the hub 120 can have a mount/handle 121 for positioning and/or fixing the hub 120 in a desired orientation relative to the target tissue (not shown).

A coil can be helical in some embodiments, and spiral in some embodiments, where a "spiral" coil can be defined as a subset of helical coils, in which a spiral coil can have changes in diameter, for example with pitch, over the length of the coil. In some embodiments, the outer coil electrode and/or the inner coil electrode can traverses through it's respective port in a helical path through the hub, the helical path of the outer coil electrode circumscribing a central axis for the outer coil, and the helical path of the inner coil electrode circumscribing a central axis for the inner coil. The central axis of the outer coil, the central axis of the inner coil, and the central axis of each guide needle are at least substantially parallel to each other, such that the each of the inner coil and the outer coil will follow the path established by the guide needles in a predictable and straight trajectory at every turn of the coils as they penetrate the target tissue. The guide needles anchor the target tissue to avoid rotation of the tissue and deflection of the coil tip, or deflection of the prostate, as the coil tip is screwed into the target tissue. Once the outer coil is advanced far enough so that it encases the target tissue, for example, the inner coil can then be inserted, in some embodiments. The helical grooves can also function to lock the axial position of the electrodes, the coils or the threaded straight needle, as discussed herein, wherever the user of the device places it, in some embodiments, rotating the coils or the threaded straight needle to change the relative axial position of each of the electrodes.

Figure 4:
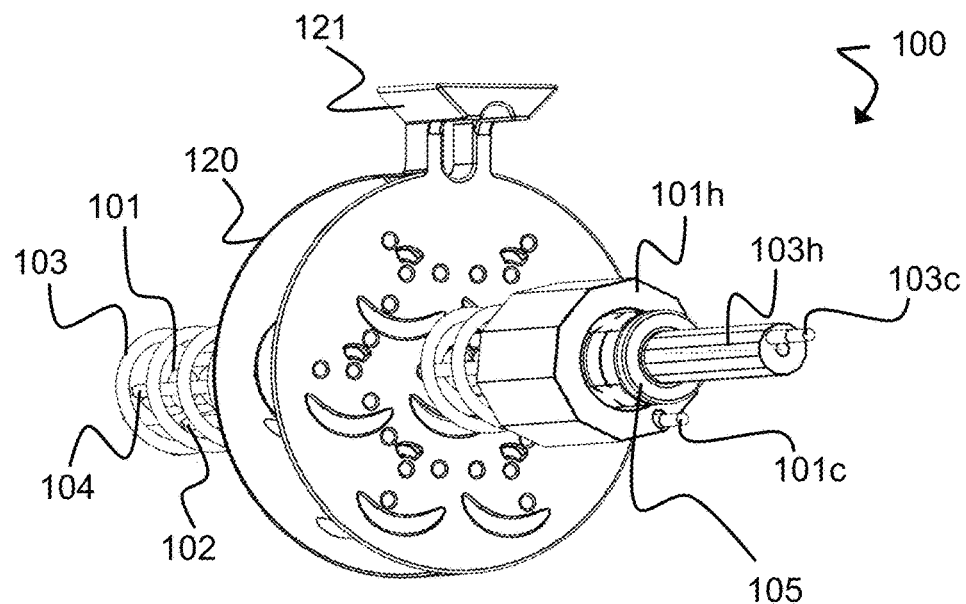
FIG. 4 is perspective view of an ablation device with a control handle assembly from the point of view of a user of the device, according to some embodiments.

As shown in FIG. 3, an ablation device provided herein, such as ablation device 100, can be even further improved in that it can be configured to have an outer coil electrode handle 101h in an operable connection with the outer coil electrode 101 and configured for adjusting the depth of the outer coil electrode 101 in the tissue (not shown); and, an inner coil electrode handle 103h in an operable connection with the inner coil electrode 103 and configured for adjusting the depth of the inner coil electrode in the tissue (not shown). In some embodiments, a depth gauge 105 can be provided in the handle assembly with visible markers to help the user determine, for example, a relative depth between the outer coil electrode 101, the inner coil electrode 103, and the guide needles 102, 104, 106 (optionally) in the tissue (not shown). The handles have ports for extensions of power source connectors for the outer coil electrode connector 101c and the inner coil electrode connector 103c. FIG. 4 is perspective view of an ablation device with a control handle assembly from the point of view of a user of the device, according to some embodiments.

Figure 5:
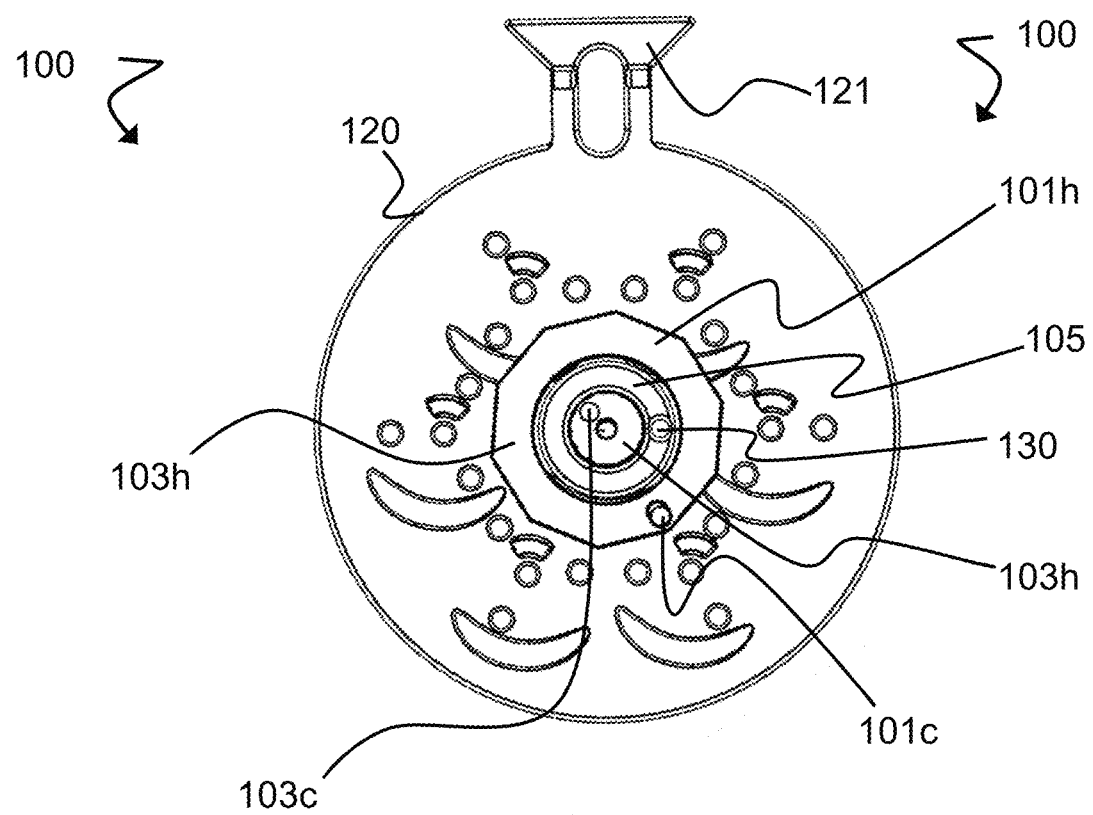
FIG. 5 is plan view of an ablation device from the end having the control handle assembly, according to some embodiments.
Figure 6:
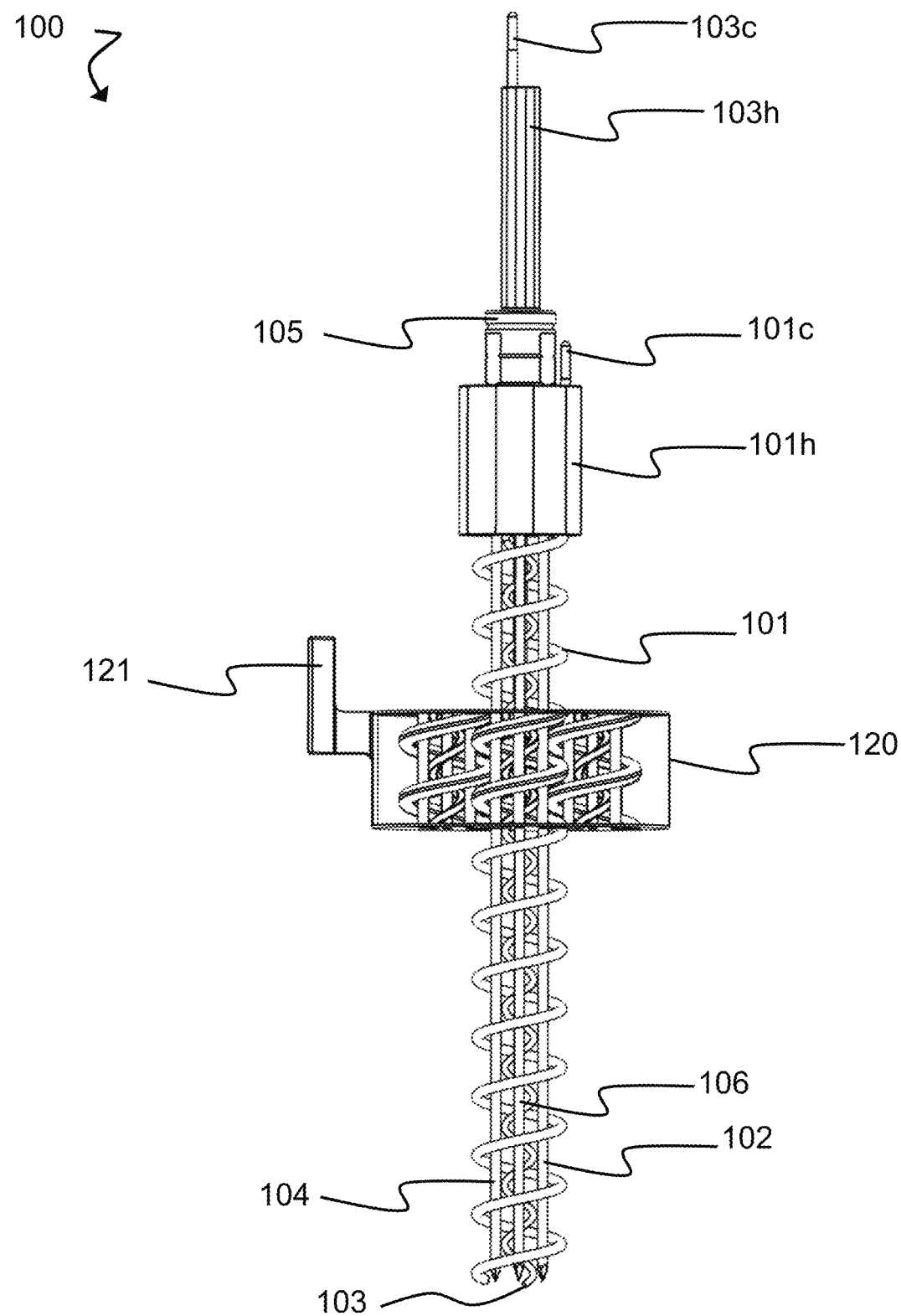
FIG. 6 is lateral view of an ablation device having the control handle assembly, according to some embodiments.

FIG. 5 is plan view of an ablation device from the end having the control handle assembly, according to some embodiments. As shown in FIG. 5, an indicia pin 130 can be included in depth gauge 105 to help orient the position of a guide needle 102, 104, 106 in a desired location relative to the hub 120, such that the other guide needle(s) are also oriented in a desired position, accordingly. FIG. 6 is lateral view of an ablation device having the control handle assembly, according to some embodiments.

The handles can be placed in any configuration desired by the skilled artisan. In some embodiments, the handles on each electrode or needle can be configured in positions that are concentric to each other to help ensure that each component that is inserted into the tissue remains concentric and aligned. In some embodiments, the innermost component to be inserted can have the longest handle, and each handle progressing to the outermost handle each gets gradually shorter as the component diameter becomes bigger. In such embodiments, the user of the ablation device can have access to all handles at any stage in the procedure for more flexibility in the workflow.

Rigid Inner Ablation Coils with a Straight Shaft

Figure 7:
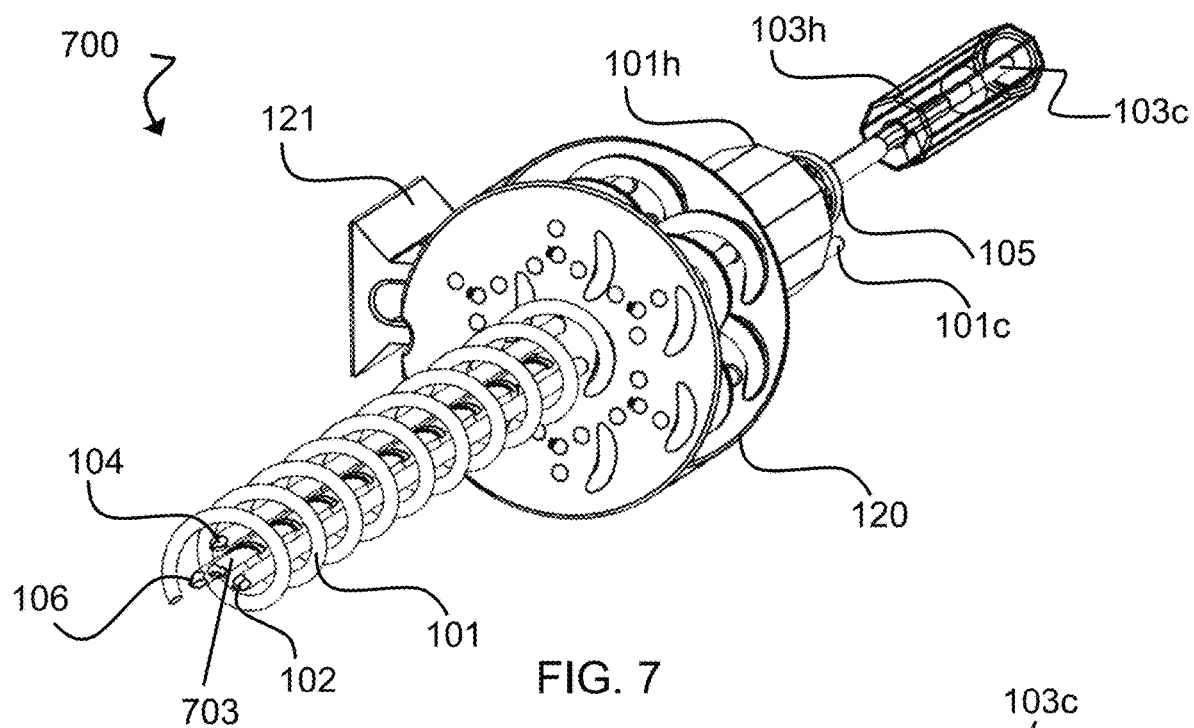
FIG. 7 is perspective view of an ablation device with a control handle assembly, the inner coil having a solid core, according to some embodiments.
Figure 8:
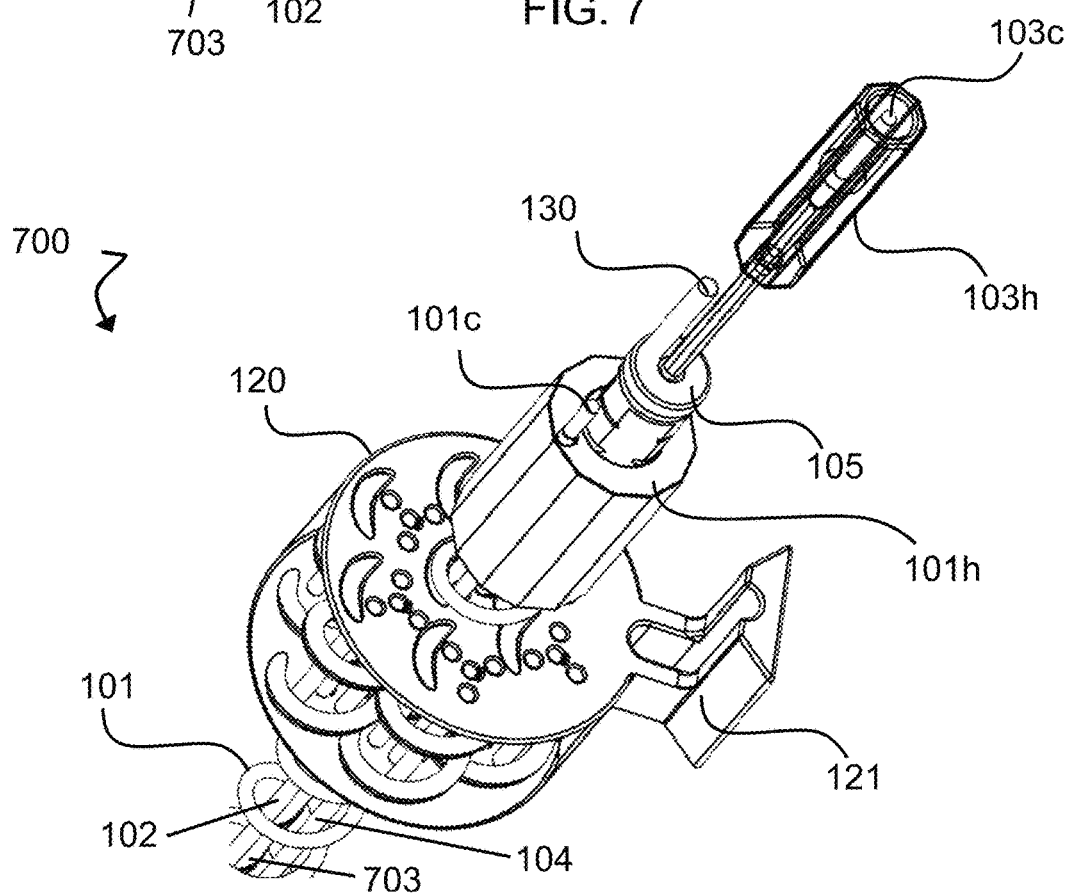
FIG. 8 is perspective view of an ablation device with a control handle assembly from the perspective of a user, the inner coil having a solid core, according to some embodiments.
Figure 9:
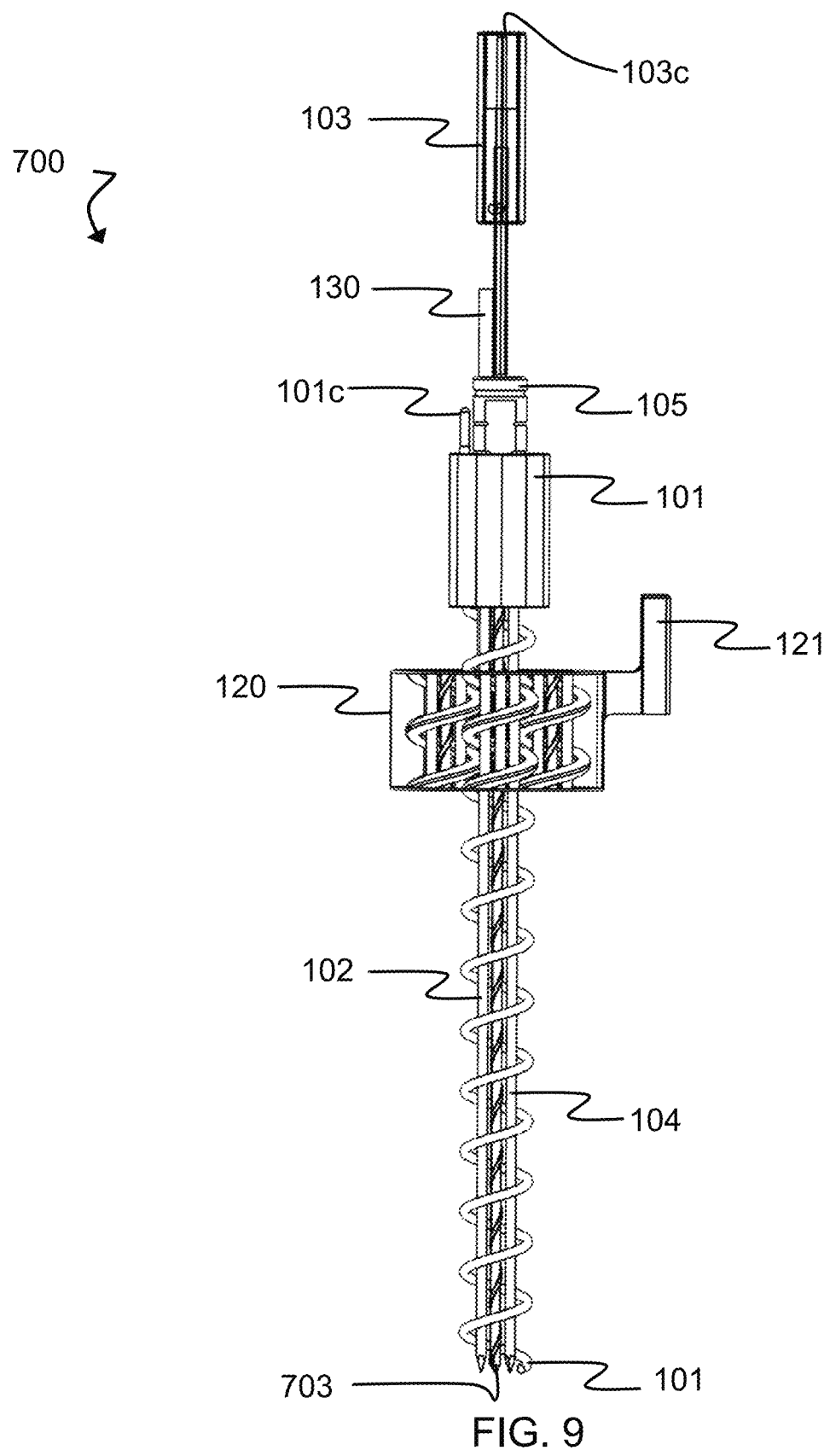
FIG. 9 is lateral view of an ablation device having the control handle assembly, the inner coil having a solid core, according to some embodiments.

The devices are even further improved in that they can be configured to have an inner coil with a lumen and, in some embodiments, the inner coil can have a straight shaft. In some embodiments the straight shaft has a solid core and, in some embodiments, the straight shaft does not have a solid core. However, in some embodiments, the inner coil can be replaced with an inner electrode that is not helical at all, but rather a straight needle. However, in some embodiments, the inner coil is a needle with a spiral conductor wrapping around the straight shaft, such that the spiral conductor is a basis for defining it as an inner "coil". FIG. 7 is perspective view of an ablation device with a control handle assembly, the inner coil having a solid core, according to some embodiments. In FIG. 7, ablation device 700 has an inner coil 103 with a straight shaft. Otherwise, the components of ablation device 700 are similar those of ablation device 100 discussed above, and so these other components will not be discussed again in this section. In some embodiments, the inner coil 103 is a spiral conductor, such that the spiral conductor has a conductive spiral protrusion. And, in some embodiments, the straight shaft of inner coil 103 can be a non-conducting material, such as an insulator material, or at least substantially non-conductive relative to the spiral conductor. Moreover, in some embodiments, the solid core can be radiolucent, or at least substantially radiolucent. Such an inner coil, for example, can provide a small diameter with sufficient strength to penetrate a target tissue without undue deformation, and sufficient conductivity to provide sufficient energy for the ablation. FIG. 8 is perspective view of an ablation device with a control handle assembly from the perspective of a user, the inner coil having a solid core, according to some embodiments. FIG. 9 is lateral view of an ablation device having the control handle assembly, the inner coil having a solid core, according to some embodiments.

The outer electrode and the inner electrode of the ablation device can be configured in any manner deemed suitable to one of skill, including wire diameter, outer diameter of the coil, and the inner diameter of the coil.

The inner electrode, in some embodiments, can simply be a coil that has an outer diameter than is smaller than the inner diameter of the outer coil. In some embodiments, the inner coil can be a straight needle, or perhaps a straight needle with helical flute-threads on the outer surface. In some embodiments, an inner ablation coil electrode can have an outer diameter that ranges from about 0" to about 0.5" in distance away from the inner surface of the guide needles, or that ranges from about 0.005" to about 0.125" from the inner surface of the guide needles, so that the guide needle can guide the inner coil accurately and precisely toward the target tissue. The guide needles can also keep the coils at least substantially parallel for the increased uniformity of energy distribution during ablation, as described herein. Moreover, in some embodiments, a single, straight needle can be inserted into the target tissue along the center axis of the outer coil to guide the inner coil into the target tissue, inside of the outer coil, if the inner coil has a sufficiently small diameter. In these embodiments, for example, the inner diameter of the inner coil can range from about 1.1 to 4 times, about 1.1 to 3.5 times, or 2 to 3 times larger than the outer diameter of the center guide needle. In some embodiments, the inner diameter of the inner coil can be 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or any amount therein in amounts of 1%, larger than the outer diameter of the center guide needle.

In some embodiments, the inner electrode can be a straight needle with helical flute-threads or grooves at the distal section. In some embodiments, the inner electrode can have solid core diameter that is small like a needle, having a minor diameter of the core of no more than about 0.063", to minimize resistance to insertion in tissue, and minimize trauma, but remain stiff enough to resist bending by increasing the other diameter, or major diameter, through the thickness of the flute-threads. In some embodiments, the major diameter can be from about 10% to about 100% larger than minor diameter of the core. In some embodiments, the major diameter can be from about 20% to about 50% larger than the minor diameter of the core. In some embodiments, the major diameter can be 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or any amount therein in amounts of 1%, larger than the minor diameter of the core. This extra stiffness allows the physician to insert this electrode like a needle through the center hole on the guide on the center axis of the outer coil and be straight and concentric to outer coil throughout insertion to target tissue. The sharp tip is also centered on the axis of the needle so that it centers itself as it is pushed in and does not veer sideways. The flute-threads can also help drive the needle into tough tissue as the user can rotate the needle in same sense of helix of the flute-thread to help drive the tip forward for easier penetration into tissue. Once the destination is reached the flute-thread can act as axial anchor to provide positional stability of the needle. Finally, the flute-threads provide more surface area for distributing current density than a straight needle so there will be more uniform heating of tissue overall, and less current density near the inner electrode, which is not beneficial. There can be a helical groove in the guide at the center to anchor the axial position of the flute-threaded needle.

Improved Energy Density Profiles

The devices are even further improved in that they can be configured for an improved energy density profile to improve ablation. For example, in some embodiments, the dual coil ablation systems can include a phase-offset between the coils as a further significant improvement to achieve a surprising enhancement to the energy density provided by the systems for the ablation which also, as a result, provides a further significant and surprising enhancement to the speed and/or uniformity of ablation achieved. The term "phase" is referred to herein as a representation, a model for comparison merely based on "wave" terminology, of the relative displacement between the coils, the displacement analogous to the displacement of waves, for example, by comparing a side view of the position of the inner helical coil electrode relative to the position of the outer helical coil electrode. Just as waves displaced relative to one another, particularly those having the same frequency, can have a "phase difference", the inner helical coil electrode can have a phase difference relative to the outer helical coil electrode. The phrase "phase difference" can be used synonymously with "phase offset", in some embodiments.

A leading phase refers to a wave (or a first coil in this case) that is displaced "ahead" of another wave (second coil). Lagging phase refers to a wave (or a first coil in this case) that is displaced "behind" of another wave (second coil). When the waves (or coils) differ in phase by −90° or +90° they are said to be in phase quadrature. When the waves (or coils) differ in phase by −180 degrees or +180° degrees, the waves (or coils) are said to be in phase opposition. For purposes of the teachings herein, whether lagging or leading, a negative phase offset is equal to a positive phase offset. For example, an offset of −30° is technically the same as an offset of +30°, an offset of −180° is technically the same as an offset of +180°, and so on. When comparing the inner helical coil electrode and the outer helical coil electrode, for example, the pitch of the outer coil can be the same as the pitch of the inner coil, and the phase-offset is measured by comparing the relative "wave" positions of the coils from a side view as they are positioned relative to one another. In some embodiments, for example, the outer pitch is positioned to have a phase-offset with respect to the inner pitch, the phase-offset ranging from between 30° to 180°. If the pitch of the inner coil does not match the pitch of the outer coil, for example, the phase-offset can vary along the length of the coils as they are positioned relative to one another. In such embodiments, the phase-offset can be an average of the phase offset that is experienced along the length of the coils as they are positioned relative to one another. For this reason, in some embodiments, where the pitches of the inner coil and outer coil are different, the average of the phase offset along the length of the coils as they are positioned relative to one another can be phase-offset ranging from between 30° to 180°.

Figure 10:
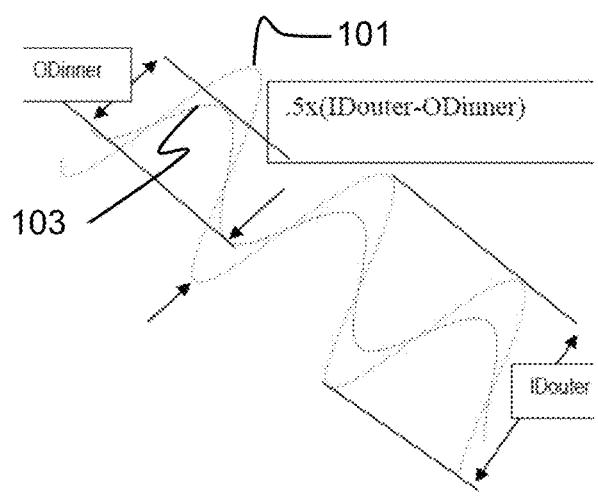
FIG. 10 is an illustration of a dual coil arrangement with little-to-no phase offset, according to some embodiments.

FIG. 10 is an illustration of a dual coil arrangement with little-to-no phase offset, according to some embodiments. As illustrated in FIG. 10, outer ablation coil 101 is essentially an outer waveform, and inner ablation coil 103 is essentially an inner waveform, and the peaks and troughs of the waves can be in or out of phase with each other. In FIG. 10, for example, the peaks and troughs of the waves are essentially in-phase, or have little-to-no, or substantially no, phase-shift, also referred to herein as "phase-offset," relative to one another. In FIG. 10, the phase-offset would be considered to be about 0° offset.

Figure 11:
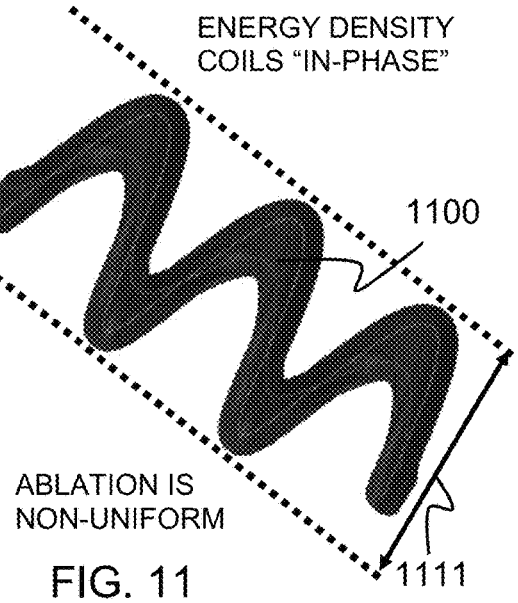
FIG. 11 is an illustration of a helical energy density from a dual coil arrangement with little-to-no phase offset, accordingly to some embodiments.

FIG. 11 is an illustration of a helical energy density from a dual coil arrangement with little-to-no phase offset, accordingly to some embodiments. As illustrated in FIG. 11, the in-phase relationship between outer ablation coil 101 and inner ablation coil 103 provides an energy density 1100 that also exists in a sort of "waveform" shape, meaning that the ablation energy applied to a target tissue 1111 from the in-phase relationship creates an energy density profile that would be expected to ablate less uniformly across the target tissue 1111.

Figure 12:
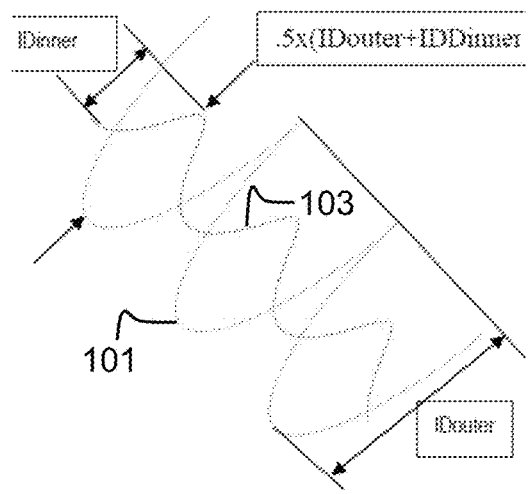
FIG. 12 is an illustration of a dual coil arrangement with significant phase offset, according to some embodiments.

FIG. 12 is an illustration of a dual coil arrangement with significant phase offset, according to some embodiments. In FIG. 12, for example, the peaks and troughs of the waves are essentially out-of-phase, or have phase-shift, also referred to herein as "phase-offset," relative to one another. In FIG. 12, the phase-offset would be considered to be about 180° offset.

Figure 13:
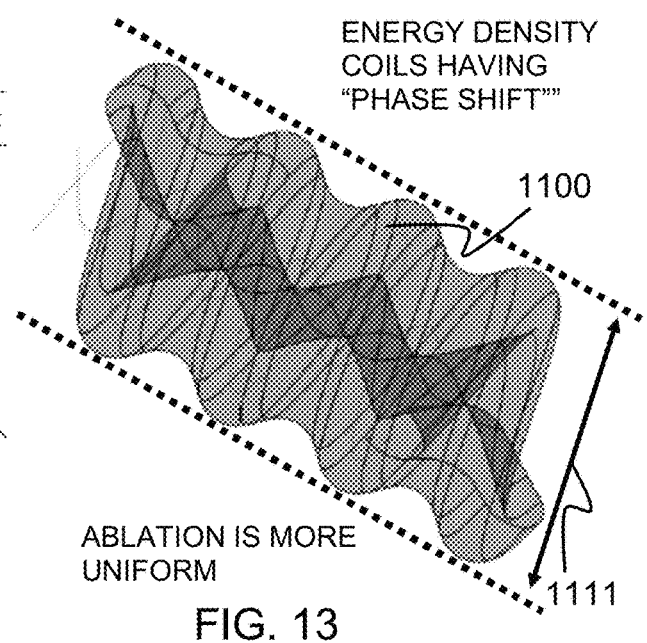
FIG. 13 is an illustration of a helical energy density from a dual coil arrangement with significant phase offset, accordingly to some embodiments.

FIG. 13 is an illustration of a helical energy density from a dual coil arrangement with significant phase offset, accordingly to some embodiments. As illustrated in FIG. 13, the out-of-phase relationship between outer ablation coil 101 and inner ablation coil 103 provides an energy density 1100 that exists in a more uniform shape or application of ablation energy, meaning that the ablation energy applied to a target tissue 1111 from the phase-offset relationship creates an energy density profile that would be expected to ablate with more uniformity across the target tissue 1111, providing an improved energy density profile and ablation efficacy.

As such, in some embodiments, the outer coil has an outer pitch, the inner coil has an inner pitch, and the outer pitch is positioned to have a phase-offset with respect to the inner pitch, the phase-offset ranging from between about 10° to about 180°, about 15° to about 180°, about 20° to about 180°, about 25° to about 180°, about 30° to about 180°, about 35° to about 180°, about 40° to about 180°, about 45° to about 180°, about 50° to about 180°, about 55° to about 180°, about 60° to about 180°, about 65° to about 180°, about 70° to about 180°, about 75° to about 180°, about 80° to about 180°, about 85° to about 180°, about 90° to about 180°, about 95° to about 180°, about 100° to about 180°, about 105° to about 180°, about 110° to about 180°, about 115° to about 180°, about 120° to about 180°, about 125° to about 180°, about 130° to about 180°, about 135° to about 180°, about 140° to about 180°, about 145° to about 180°, about 150° to about 180°, about 155° to about 180°, about 160° to about 180°, about 165° to about 180°, about 170° to about 180°, about 175° to about 180°, or any range or amount there in increments of 1°. As such, one of skill will appreciate that the phase offset can be for example, about 10°, about 20°, about 30°, about 40°, about 50°, about 60°, about 70°, about 80°, about 90°, about 100°, about 110°, about 120°, about 130°, about 140°, about 150°, about 170°, about 180°, or any amount therein in increments of 1°. The phase-offset may also be expressed as a fraction of the "pitch", for example, such that the outer coil and the inner coil can also be out of phase from 0.1×Pitch, 0.2×Pitch, 0.3×Pitch, 0.4×Pitch, 0.5×Pitch, 0.6×Pitch, 0.7×Pitch, 0.8× Pitch, 0.9×Pitch, or any range of Pitch fraction therein in increments of 0.1×Pitch, in some embodiments. It should also be appreciated that the phase-offset can be fixed, in some embodiments, or it can be adjustable as an added control.

As with the guide needles, the phase-offset can also have the advantage of avoiding having the inner and outer electrodes from coming too close to one another or contacting one another. Those of skill will appreciate that the phase-offset between the coils can further help to avoid undesirable situations in which the inner ablation electrode and the outer ablation electrode either come too close together due to bending, or even make contact, causing a short, either situation of which can cause the ablated tissue to over-necrose. Again, as noted above, if the inner ablation electrode is close to the outer ablation electrode, tissue on the opposite side of the inner electrode may be correspondingly under-ablated, or will not achieve necrosis, potentially not achieving cell death inside the target area of the distal part of the outer coil. Over-necrosed tissue can adhere to the electrode surface, which is undesirable, as it will have a high impedance and affect how the conducts and ablates the adjacent tissue Multi-Pattern Guide Templates The systems can be even further improved by facilitating a pattern of ablations that can expand the amount and/or shapes used to ablate the tissue. In some embodiments, for example, the hub is a multi-pattern guide template further comprising n additional ablation templates, where n is the number of ablation on the hub, n ranging from 1 to 10. One of skill will appreciate that the plurality of the ablation templates can be used to create a plurality of ablation patterns to ablate the tissue.

Figure 14:
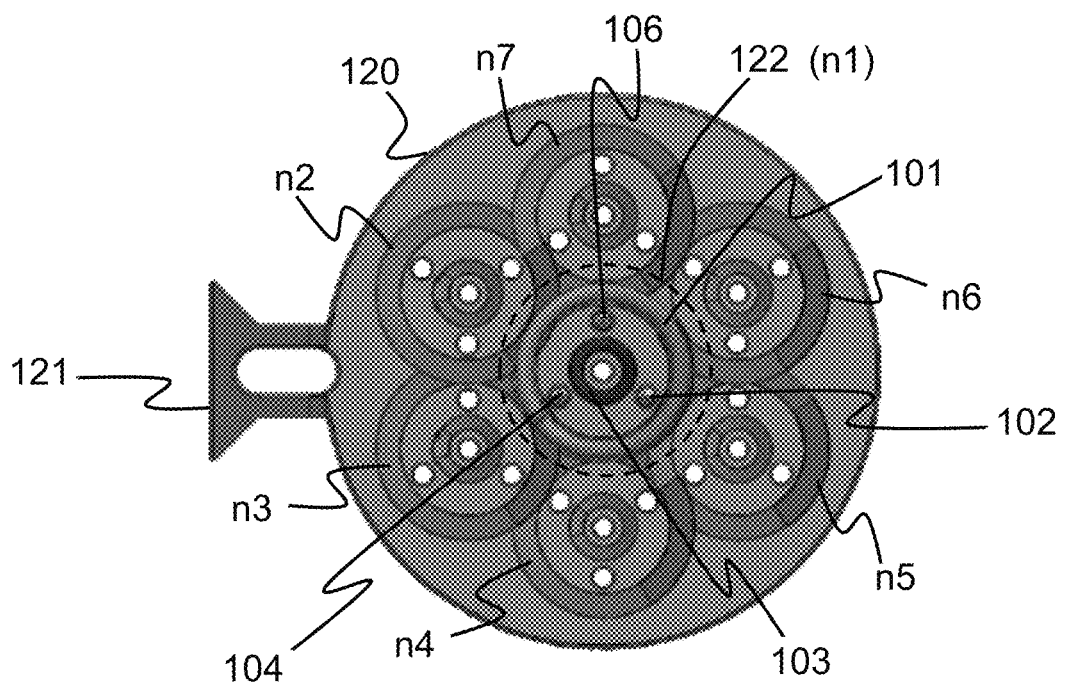
FIG. 14 is a plan view of a multi-pattern guide template, the inner coil having a lumen, according to some embodiments.

FIG. 14 is a plan view of a multi-pattern guide template, the inner coil having a lumen, according to some embodiments. As shown in FIG. 14, the first ablation template 122, also referred to as "n1", is accompanied by 6 additional templates, such that "n=6" in this embodiment, for a total of 7 templates available, for use alone or in any combination. The multi-pattern guide template has an inner coil 103 with a lumen.

Figure 15:
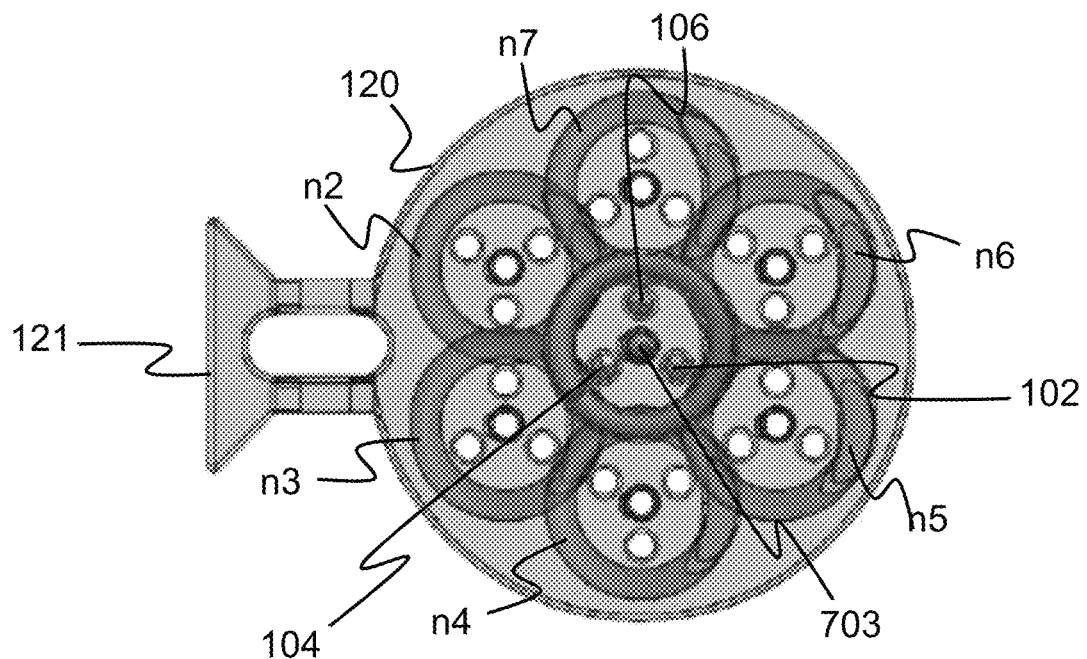
FIG. 15 is a plan view of a multi-pattern guide template, the inner coil having a solid core, according to some embodiments.

FIG. 15 is a plan view of a multi-pattern guide template, the inner coil having a solid core, according to some embodiments. As shown in FIG. 15, similar to FIG. 14, the first ablation template 122, also referred to as "n1", is accompanied by 6 additional templates, such that "n=6" in this embodiment, for a total of 7 templates available, for use alone or in any combination. The multi-pattern guide template has an inner coil 703 with a solid core.

Any arrangement of template positions can be used, and can be designed for a particular procedure or set of procedures. In some embodiments, for example, any combination of ablations can be performed around the template to form a variety of ablation sizes and shapes, from round to rectangular, to semicircular, and the like. Regardless, the skilled artisan will appreciate, for example, a system that uses guide needles to hold the target tissue, and a multi-pattern guide template, will result in less gaps between the single ablations in the multi-pattern ablations, facilitating the overall desired ablation target of tumor and margin. If the target tissue is a prostate tissue, for example, the target (prostate) is mechanically fixated while you change pattern, thus avoiding potential gaps that could arise if the target was allowed to move during insertion.

Self-Tapping Guide Needles and Self-Centering Guide Needles for Ease of Fixation of Tissue for Ablation The systems can be even further improved through the addition of self-tapping tips on the guide needles, for example, in order to ease penetration of target tissue by a user of the system. The systems can be even further improved through the addition of self-centering tips on the guide needles, for example, in order to ease maintaining the intended direction of penetration of target tissue by a user of the system. Any tip design that will provide a self-centering or a self-tapping function can be used, for example, in order to facilitate ease of penetration, or ease of maintaining the intended direction of penetration, of target tissue by a user of the system.

Figure 16:
FIG. 16 is a lateral view of the distal end of a self-tapping guide needle, according to some embodiments.

FIG. 16 is a lateral view of the distal end of a self-tapping guide needle, according to some embodiments. One of skill will appreciate that there are several self-tapping configurations available, any of which that the artisan deems suitable for the type of tissue penetrated, and the gauge of the guide needle, can be used in some embodiments.

Computerized and Robotic Systems

Computerized and robotic systems are also provided by the teachings herein. The mechanical device can be controlled by a computer, including a database, modules, and/or engines with instructions for execution by a processor, the database, modules and or engines on a non-transitory computer readable storage medium, for example, in order to accomplish robotic and/or remote control for precise and accurate positioning of the ablation device relative to the tissue of the subject. Any suitable processor and memory known to one of skill in the art can be used in the design and configuration of such a robotic system. In some embodiments, the systems can include a positioning module on a non-transitory computer readable storage medium, the positioning module configured to move the ablation device in the X, Y, and/or Z directions. In some embodiments, the positioning module can also rotate the ablation device about the X, Y, and Z axes to establish the desired vector of approach in space for the ablation of tissue in a subject. In some embodiments, the desired vector of approach is correlated with imaging that is used in the location of the tissue to be ablated.

In some embodiments, the systems can include a fixation module on a non-transitory computer readable storage medium, the fixation module configured to guide the needles 102, 104, 106 on the direction of approach of the needles 102, 104, 106 into the target tissue (not shown), the location of the target tissue for insertion of the needles 102, 104, 106, and/or the depth of insertion of each of the needles 102, 104, 106 into the subject, for example, in order to fixate the target tissue for the insertion of the outer ablation coil 101 and the inner ablation coil 103, and establish guides for an accurate and precise insertion of the outer ablation coil 101 and the inner ablation coil 103 into the target tissue. In some embodiments, the computerized and/or robotic systems can include a depth module on a non-transitory computer readable storage medium, in which the relative positioning of the guide needles 102, 104, 106, the outer coil 101, and the inner coil 103, as well as the phase-offset between the outer coil 101 and the inner coil 103, can be controlled by the depth module. The phase offset can range from 30° to 180°, for example.

In some embodiments, the systems can include an ablation module on a non-transitory computer readable storage medium for activating the ablation device to ablate tissue, wherein the ablation module can be programmable for any number of parameters, for example, to adjust the dwell time of the ablation, the power applied to the ablation device, or both, and this programming can be set for any tissue or procedure of interest, in some embodiments. In some embodiments, "dwell time" can selected as the duration time of the ablation at a select energy of ablation, and, in some embodiments, "dwell time" can be a combination of the energy of ablation as it is applied, and/or varied, over the duration time, for example. In some embodiments, the programming of these variables may be based on feedback such as impedance and temperature of tissue wherein proportional integral derivative (PID) control can be used in real time. In addition, the ablation module and/or the depth module can coordinate with the positioning module in the control of the activation of the ablation device, such that the ablation module is inactive, or at least the power is not applied to the ablation device, until the positioning module and/or the depth module has completed the positioning of the ablation device 100,700, the guide needles 102, 104, 106, outer coil 101 and/or inner coil 103, in some embodiments.

The ablation module and the depth module can each be used to program and control the use and positioning of a plurality of coil combinations to ablate tissue in a desired shape and configuration, in the X, Y, and or Z directions, so that the ablation can be robotically controlled to ablate a tissue in a desired three-dimensional pattern. One of skill in the art of robotics will appreciate that, much like a 3D printer creates a 3-D material of a desired shape, the systems, devices, and methods provided herein can be programmed to ablate-away tissue having a desired 3D shape. In one embodiment, an optimized navigation plan is used such that multiple guide needles, either selected from a fixed selection of guide needle sets with a preset configuration, or not in a preset configuration, are optimally placed specific to the target ablation plan. Subsequently, the optimal outer and inner coils, sized appropriately for the guide needle configuration, are selected and screwed into place.

User Feedback Through Impedance

Likewise, the systems and methods provided herein can include feedback to the user to enhance the user's experience in the ablation of tissue, as well as reduce the risk and time involved in performing the procedures. For example, in some embodiments, the systems can further comprise one ore more impedance electrodes operable to provide a feedback response for navigating the penetration of components of the systems into the tissue for ablation, the navigating including monitoring the electrical impedance of the tissue.

Impedance can be monitored in the navigation of the systems taught herein, for example, to monitor the position of the needles and/or coils and/or electrodes as each of them are advanced into a subject, wherein the impedance values can indicate the position of the conductive tips of any of these components. This can help, for example, during needle placement. The idea is that the target tissue can have different impedance readings as compared to the surrounding tissue. The feedback can be audible, as the volume or pitch of sound can be used to notify the user of the ablation device of the different impedance levels while the needles and/or coils and/or electrodes are advanced. The use of audible feedback is desirable, as it allows the user of the ablation device to focus his eyes on a direct visualization or other imaging modalities, such as ultrasound. Likewise, since impedance reflects a difference between tissue types, impedance values can be used separately as feedback determine the degree of tissue ablation or necrosis to further navigate the progress of the procedure. A rapid impedance increase, for example, can be used to indicate that a tissue is close to complete ablation or necrosis. One of skill will appreciate that there is value in this ability to navigate device components, particularly in knowing where you are in the tissue, as this knowledge may help in avoiding critical structures (nervous tissue, urethra, bowel, exiting prostate capsule unintentionally), or it may help in refining or optimizing where the target ablation tissue is, as the impedance can provide such useful feedback as the needle and/or coil or electrode tip enters the tissue such as, for example, a cancerous tissue.

As such, the ablation devices taught herein can be designed to include one or more impedance feedback component that can be configured to provide any feedback that is considered to be useful in the ablation procedure. In some embodiments, the ablation system further comprises an impedance electrode or electrodes operable to provide a feedback response for monitoring the electrical impedance of the tissue near the tip, as the feedback response helps the user of the system to navigate a component of the system in the tissue. In some embodiments, the methods can include monitoring the position of the first guide needle and/or the second guide needle, wherein the ablation system further comprises an impedance electrode or electrodes operable to provide a feedback response for monitoring the electrical impedance of the tissue near the tip to navigate the penetration of the first guide needle and/or second guide needle in the tissue. Likewise, the methods can include monitoring the position of the inner coil electrode or the outer coil electrode to navigate the penetration of the first guide needle and/or second guide needle in the tissue. Moreover, in some embodiments, the impedance electrode can be operable to provide a feedback response for monitoring the electrical impedance of a tissue to determine the extent of ablation, which may be, for example, in the annular ablation region. In this way, the user can navigate the progress of the ablation procedure, in addition to navigating the position of the system components during the procedure. The feedback response, for example, can include an audible response and/or tactile feedback, in some embodiments.

It should be appreciated that the inner electrode, which can be the inner helical electrode, and the outer helical electrode can each also function as an impedance electrode, in some embodiments.

Methods of Using the Ablation Devices and Systems

Methods of using the devices are also provided. A user of the devices, systems, and methods provided herein will appreciate that the methods surprisingly enhance the quality of ablation technologies by at least, (i) improving the accuracy of the placement of the electrodes into the tissue by securing the tissue to be ablated with a plurality of guide; (ii) improving the accuracy of the placement of the electrodes into the tissue by guiding the placement of the electrodes with the plurality of guide needles including, for example, improving the accuracy and precision in obtaining concentric ablation coils when positioning the ablation devices for a procedure; (iii) improving the versatility of the system by allowing a user to select sizes and shapes of regions to be ablated through the use of a multi-pattern guide template; and (iv) improving the energy density distribution through the use of a phase-offset configuration between the coil electrodes. One of skill will appreciate that these improved methods can include one or more impedance feedback components to tell the user of the ablation device the type of tissue in which the electrodes are located, and the extent of ablation achieved. Regardless of the user of the devices, systems, or methods, those of at least ordinary skill in the art will appreciate that these improvements add significant value to the field of ablation technologies, making it easier, more cost-effective, and less risky to perform ablation procedures.

Figure 17:
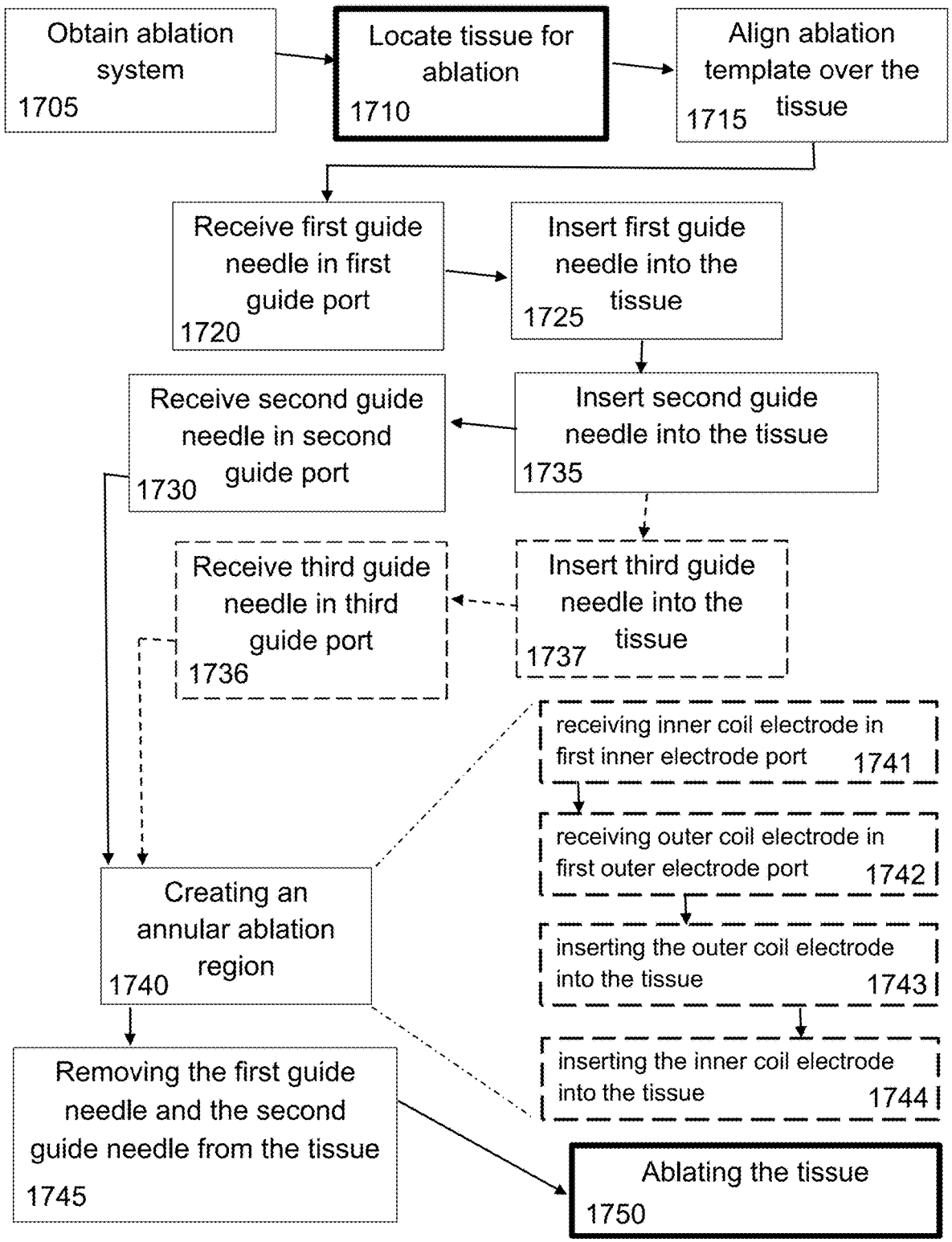
FIG. 17 is a flowchart of a method of ablating a tissue, according to some embodiments.

FIG. 17 is a flowchart of a method of ablating a tissue, according to some embodiments. In some embodiments, the methods can include obtaining 1705 any of the ablation systems taught herein which can include, for example, an ablation system having an inner coil electrode with an outer surface and an inner pitch, an outer coil electrode with an inner surface and an outer pitch, a first guide needle with a first guide axis, a second guide needle with a second guide axis. As noted, the systems can also include a hub having a first ablation template with a first outer electrode port adapted for receiving the outer coil electrode, a first inner electrode port adapted for receiving the inner coil electrode, a first guide port for receiving the first guide needle, and a second guide port for receiving the second guide needle.

The process will include locating 1710 a tissue for ablation, also referred to as a "target tissue". Another step includes aligning 1715 the first ablation template over the tissue. Another step includes receiving 1720 the first guide needle in the first guide port of the first ablation template. The first guide needle is inserted 1725 into the target tissue. The methods can include receiving 1730 the second guide needle in the second guide port of the first ablation template. And, of course, the method can also include inserting 1735 the second guide needle into the target tissue.

To further improve the systems, in some embodiments, the systems can also include a plurality of guide needles that further include a third guide needle having a third guide axis and a third guide length. The annular ablation region can also be around the third guide needle with the third guide axis in an at least substantially parallel arrangement with the first guide axis with the second guide axis. Moreover, the first ablation template can be configured to further include a third guide port for receiving the third guide needle. As such, the methods can include receiving 1736 the third guide needle in the third guide port of the first ablation template. And, of course, the method can include inserting 1737 the third guide needle into the target tissue.

The methods can include creating 1740 an annular ablation region in the tissue to be ablated. The creating 1740 can include receiving 1741 the inner coil electrode in the first inner electrode port of the first ablation template; receiving 1742 the outer coil electrode in the first outer electrode port of the first ablation template; and, inserting 1743 the outer coil electrode into the tissue. In some embodiments, the inserting 1743 can include slidably translating the luminal surface of outer coil electrode around the first guide needle and the second guide needle, wherein the outer coil electrode contains the first guide needle and the second guide needle. One of skill will appreciate that the inner ablation coil and the outer ablation coil can be inserted into the target tissue in any order, in some embodiments. In some embodiments, however, one of skill will prefer either inserting the inner ablation coil followed by inserting the outer ablation coil. And, in some embodiments, one of skill will prefer inserting the outer ablation coil followed by inserting the inner ablation coil.

Likewise, in some embodiments, the methods include inserting 1744 the inner coil electrode into the tissue. As such, in these embodiments, the inserting 1744 can include slidably translating the outer surface of inner coil electrode concentric, or at least substantially concentric with the outer coil electrode to create the annular ablation region. One of skill will appreciate that, given the above steps, the first guide needle and the second guide needle can be in the annular ablation region.

The methods can include removing 1745 the first guide needle and the second guide needle from the target tissue; and, ablating 1750 the tissue. One of skill will appreciate that any of the methods provided herein can include securing the tissue and guiding the dual coil ablation system into the target tissue for the ablation, the securing and the guiding facilitated by the first guide needle and the second guide needle.

Due to the presence of the inner coil and the outer coil, in some embodiments, the methods include creating an annular ablation region in the tissue to be ablated. The creating can include receiving the inner coil electrode in the first inner electrode port of the first ablation template; receiving the outer coil electrode in the first outer electrode port of the first ablation template; and, inserting the outer coil electrode into the tissue. In some embodiments, the inserting can include slidably translating the luminal surface of outer coil electrode around the first guide needle and the second guide needle, wherein the outer coil electrode contains the first guide needle and the second guide needle.

Likewise, in some embodiments, the methods include inserting the inner coil electrode into the tissue. As such, in these embodiments, the inserting can include slidably translating the outer surface of inner coil electrode concentric, or at least substantially concentric with the outer coil electrode to create the annular ablation region. One of skill will appreciate that, given the above steps, the first guide needle and the second guide needle can be in the annular ablation region.

The methods can include removing the first guide needle and the second guide needle from the target tissue; and, ablating the tissue. One of skill will appreciate that the methods provided herein can include securing the tissue and guiding the dual coil ablation system into the target tissue for the ablation, the securing and the guiding facilitated by the first guide needle and the second guide needle.

The prostate gland of a male subject is a common tissue that can be subject to an ablation in the treatment of the subject. In some embodiments, the condition is a benign prostatic hypertrophy (BPH), for example. As such, the methods can include ablating a prostate tissue of a subject and include obtaining the ablation devices and systems taught herein, locating the prostate tissue for ablation, and aligning the first ablation template over the prostate tissue to be ablated.

Figures 18, 19:
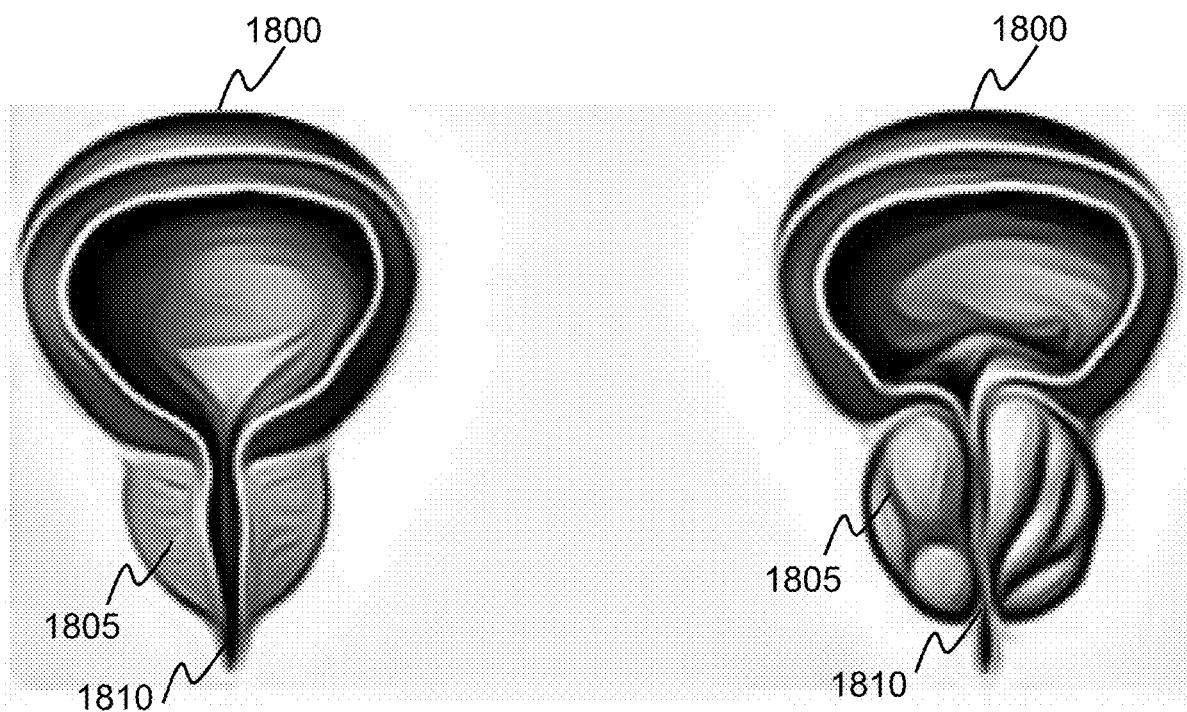
FIG. 18 is a cross-sectional illustration of a normal prostate gland, according to some embodiments.
FIG. 19 is a cross-sectional illustration of an enlarged prostate gland, according to some embodiments.

FIG. 18 is a cross-sectional illustration of a normal prostate gland, according to some embodiments. As shown in FIG. 18, the bladder 1800 empties through the urethra 1810 through a region that encompassed by prostate gland tissue 1805. Under normal circumstances, the urethra can open and empty the bladder of urine.

FIG. 19 is a cross-sectional illustration of an enlarged prostate gland, according to some embodiments. As shown in FIG. 19, the bladder 1800 cannot empty as it should through urethra 1810, as the prostate gland tissue 1805 is enlarged and is closing off the urethra. This is a common problem among men, and a treatment can include the ablation of prostate tissue using the devices, systems, methods taught herein.

In some embodiments, the method can include receiving the first guide needle in the first guide port of the first ablation template; inserting the first guide needle into the prostate tissue. In some embodiments, the methods can include receiving the second guide needle in the second guide port of the first ablation template; and, inserting the second guide needle into the prostate tissue.

Likewise, since any of the ablation systems taught herein can be used, the methods also further include the use of a third guide needle having a third guide axis; and, use of the first ablation template further includes use of a third guide port for receiving the third guide needle. As such, the methods can include inserting the third guide needle into the tissue; and, receiving the third guide needle in the third guide port of the first ablation template. It should be appreciated, given the teachings provided herein, that the inserting of the outer coil electrode into the tissue can include slidably translating the luminal surface of outer coil electrode over the first guide needle, the second guide needle, and the third guide needle. One of skill will further appreciate that the first guide needle, the second guide needle, and the third guide needle can be in the annular ablation region. And, as such, the removing can include removing the first guide needle, the second guide needle, and the third guide needle from the tissue, in some embodiments.

Moreover, the phase-offset feature can be used to significantly improve the methods taught herein. In some embodiments, the methods can include establishing a phase-offset between the outer pitch of the outer coil electrode and the inner pitch of the inner coil electrode, the phase-offset ranging from between 30° to 180°, or any offset taught herein. As such, it will be appreciated that a significantly improved ablation of the target tissue can occur within the annular ablation region formed having the phase offset between the outer coil electrode and the inner coil electrode.

The handle assemblies provided in the systems taught herein can be used to significantly ease the user of the ablation device in the ablation procedure. As such, in some embodiments, the methods can include adjusting the depth of the outer coil electrode with an outer coil electrode handle in an operable connection with the outer coil electrode; and, adjusting the depth of the inner coil electrode with an inner coil electrode handle in an operable connection with the inner coil electrode.

The impedance feedback component can be configured to provide any feedback that is considered to be useful in the ablation procedure, such as sound or tactile feedback, for example, and can be used to significantly ease the user of the ablation device in the ablation procedure. One of skill will appreciate that impedance feedback will add a layer of safety to the procedure to supplement the real-time image guidance of ultrasound, and thus help avoid critical structures. It can also be used, for example, to enhance the targeting of the target tissue, as impedance can help determine if the any component of the ablation system is in the target tissue, such as a cancerous tissue. As such, in some embodiments, the ablation system further comprising one or more impedance electrodes operable to provide a feedback response for monitoring the electrical impedance of a tissue. In some embodiments, the methods can include monitoring the position of the first guide needle or the second guide needle, wherein the ablation system further comprises or more impedance electrodes operable to provide a feedback response for monitoring the electrical impedance of a tissue. Likewise, the methods can include monitoring the position of the inner coil electrode or the outer coil electrode. Moreover, in some embodiments, the impedance electrode can be operable to provide a feedback response for monitoring the electrical impedance of a tissue to determine the extent of ablation which may be, for example, in the annular ablation region.

As discussed herein, the systems can include a hub with a multi-pattern guide template having n additional ablation templates to form a desired scope or shape of ablation, where n is the number of ablation templates and ranges from 1 to 10. Any number of templates, n, can be used. As such, in some embodiments, the methods include creating an ablation pattern to ablate the tissue with a plurality of ablation templates; and, ablating the tissue with the ablation pattern. In some embodiments, n can be 1, 2, 3, 4, 5, 6, 7, 8, 9, 10, 11, 12, 13, 14, 15, 16, 17, 18, 19, or 20.

One of skill will appreciate that anyone or any combination of the above features can be combined into the devices, systems, and methods taught herein and, accordingly, the above summary includes any one, or any combination of, such features in the technology provided herein.

Moreover, a "user" of the systems, devices, and methods taught herein can include, for example, a researcher, a physician, a veterinarian, a urologist, interventionist, and interventional radiologist, or a surgeon. Any person that ablates a tissue with the devices, systems, and methods taught herein, or any device, system, or method including the teachings provided herein, can be defined as a user.

Moreover, the methods, devices, and systems taught herein can be used on any subject for experimental purposes, or for medical treatments, for example. The terms "subject" and "patient" can be used interchangeably in some embodiments and can be used to refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like.

Moreover, terms of degree are used herein to provide relative relationships between the position and/or movements of components of the systems taught herein. For example, the phrase "substantially" and "at least substantially" can be used to refer to an approximation, perhaps relevant to an amount, position, or function one amount, position, or function relative to another. For example, an axis that is substantially, or at least substantially, parallel to another axis can be used to refer to an orientation that is intended, for all practical purposes to be parallel, but it is understood that this is just a convenient reference and that there can be variations due to stresses internal to the system and imperfections in the devices and systems. Likewise, the phrase "at least substantially parallel", "at least substantially on a plane", or "at least substantially coincident", for example, can each refer to a type of an orientation or movement that is intended, for all practical purposes, to be on or near, for example, an axis or a plane, or a point, as the case may be, as a convenient measure of the orientation or movement without having to suffer the hard definition, the ultimate measure, unless otherwise defined is known to one of skill as just a convenient reference, allowing variance until there are variations due to stresses internal to the system and imperfections in the devices and systems that affect the operation of the methods, devices and systems to the point that they are no longer of use and, in some embodiments, to the point of being non-functional. In some embodiments, the term "at least substantially parallel", "at least substantially on a plane", or "at least substantially coincident", for example, can be described as any deviation from "0°" (meaning "parallel" or "on the plane, in some embodiments), such as a deviation from the parallel or plane in an amount of about 1°, about 2°, about 3°, about 4°, about 5°, or any range or amount therein in increments of 0.1° with respect to angular deviations, and in an amount of about 1 mm, about 2 mm, about 3 mm, about 4 mm, about 5 mm, or any range or amount therein in increments of 0.1 mm, with respect to distance deviations. In some embodiments, the term "at least substantially radiolucent" can be used to refer to a material that allows radiation energy to pass through at least 50%, at least 55%, at least 60%, at least 65%, at least 70%, at least 75%, at least 80%, at least 85%, at least 90%, at least 95%, at least 99%, or any percent therein in increments of 1%. In some embodiments, the term "at least substantially radio-opaque" can be used to refer to a material that blocks radiation energy from passing through at least 50%, at least 55%, at least 60%, at least 65%, at least 70%, at least 75%, at least 80%, at least 85%, at least 90%, at least 95%, at least 99%, or any percent therein in increments of 1%. In some embodiments, the term "at least substantially conductive" can be used to refer to a material that allows current to pass through less than 50% resistance, less than 45% resistance, less than 40% resistance, less than 35% resistance, less than 30% resistance, less than 25% resistance, less than 20% resistance, less than 15% resistance, less than 10% resistance, less than 5% resistance, or any percent therein in increments of 1%.

EXAMPLES

Example 1. Data Showing that the Guide Needles not Only Fixate Tissue for Accuracy and Precision in the Ablation of the Target Tissue Itself, but they Also Add Safety by Avoiding any Undesirable Ablation of Adjacent Tissue This study provides an ultrasound viewing of the use of guide needles to position the electrodes accurately and precisely, and shows an added safety feature with the subject. That is, not only due the fact that the guide needles fixate or secure the tissue to avoid movement of the tissue during the procedure, they also guide the ablation coil electrodes into proper placement to avoid experiencing an undesired ablation of adjacent tissue.

A problem with inserting a coil under ultrasound guidance (and other image guidance) is that the coil comes in and out of view. Whereas, if you first insert guide needles, you can more easily view all needles, during the insertion, to help ensure that you are accurately placing the device at the target tissue, and in a safe zone avoiding tissue structures that are not intended to be ablated and, in fact, can be undesirably damaged. Afterwards, you follow with coil(s) which, although come in and out of view, can now be inserted reliably, in a predictable fashion due to the guide needles, adding safety to the patient during the procedure.

Example 2. Data Showing Improved Uniformity of Ablation in a Tissue from Phase-Offset Technology This study provides a comparison of an ablation of muscle tissue between an approximately 0° phase-offset and an approximately 180° phase-offset between the inner and outer ablation coil electrodes. It can be seen that the uniformity of the ablation has improved surprisingly in both the longitudinal and transverse cross-sections of the muscle tissue. Every aspect of the ablation parameters are identical between test runs, with the exception that the first run has an approximately 0° phase-offset and the second run has an approximately 180° phase-offset between the inner and outer ablation coil electrodes. The device, the power settings, the duration, and the muscle tissue source are the same.

Figure 20A:
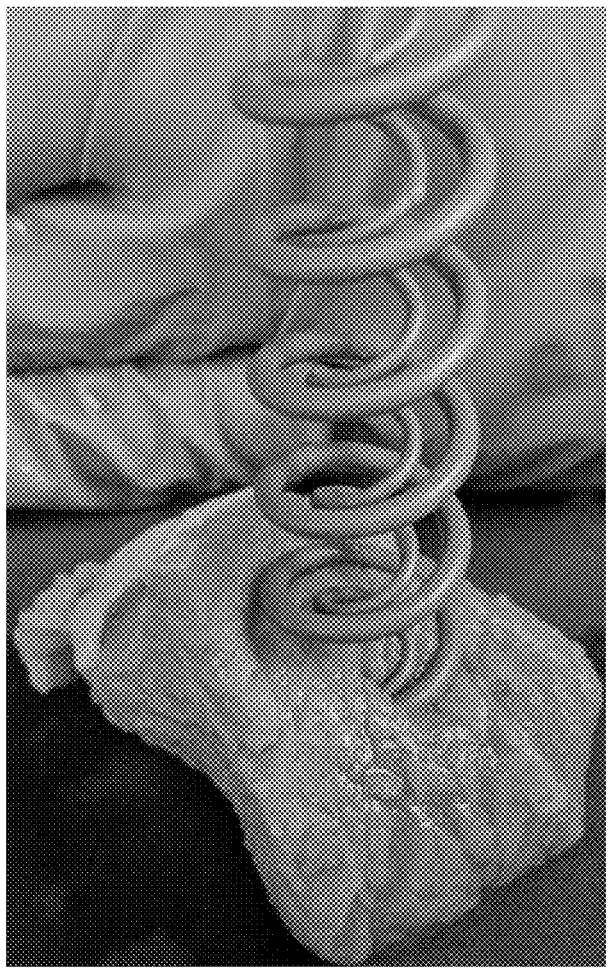
FIGS. 20A-20C show a test ablation procedure that was performed using approximately 0° phase-offset on a muscle tissue, according to some embodiments.
Figure 20B:
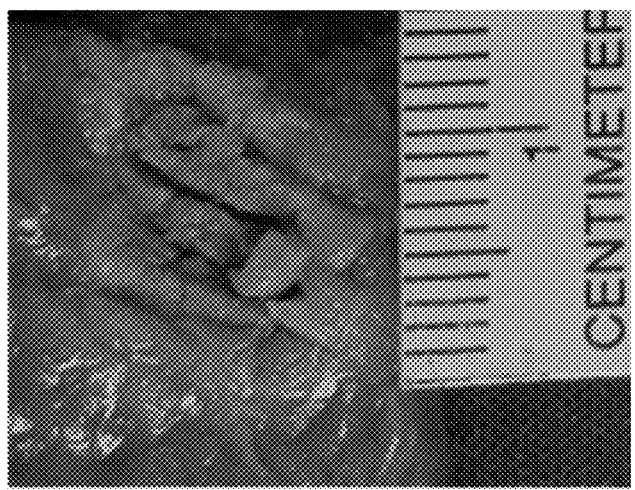
Figure 20C:
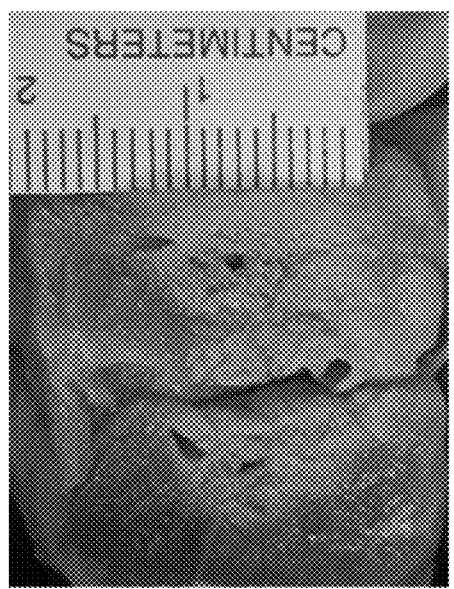

Materials and Methods:
Device: Stockert N50
Power setting: 13 Watts
Duration: 3 minutes
Muscle tissue: beef steak FIGS. 20A-20C show a test ablation procedure that was performed using approximately 0° phase-offset on a muscle tissue, according to some embodiments. FIG. 20A shows an inner ablation coil electrode aligned longitudinally with an outer ablation coil electrode, providing an approximately 0° phase-offset on the muscle tissue. FIG. 20B shows an eccentric shaped zone of ablated tissue in the transverse direction consistent with the transverse profile of the ablation energy actually applied to the tissue, and FIG. 20C shows an eccentric shaped zone of ablated tissue in the longitudinal direction consistent with the longitudinal profile of the ablation energy actually applied to the tissue.

Figure 21A:
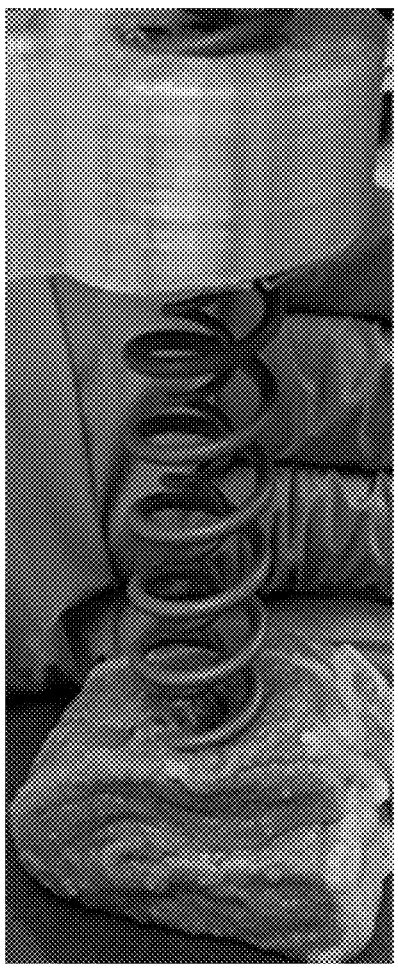
FIGS. 21A-21C show a test ablation procedure that was performed using approximately 180° phase-offset on a muscle tissue, according to some embodiments.
Figure 21B:
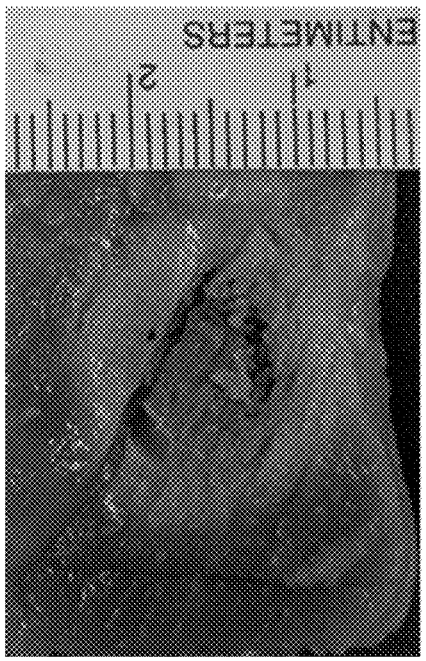
Figure 21C:

FIGS. 21A-21C show a test ablation procedure that was performed using approximately 180° phase-offset on a muscle tissue, according to some embodiments. FIG. 21A shows an inner ablation coil electrode aligned longitudinally with an outer ablation coil electrode, providing an approximately 180° phase-offset on the muscle tissue. FIG. 21B shows a uniform, round-shaped zone of ablated tissue in the transverse direction consistent with the transverse profile of the ablation energy actually applied to the tissue, and FIG. 21C shows a uniform, cylindrical-shaped zone of ablated tissue in the longitudinal direction consistent with the longitudinal profile of the ablation energy actually applied to the tissue.

As can be seen from the test data, the ablation energy actually applied to the muscle tissue with the 180° phase offset was surprisingly more uniform in both the transverse and longitudinal directions than the ablation energy actually applied to the muscle tissue with the 0° phase offset. One of skill in the art will appreciate the unexpected and substantial increase in uniformity that was observed through the phase-offset of the inner and outer ablation coils.

Example 3. Workflow Possibilities

A number of workflow possibilities are availability when using the systems and methods taught herein. The choice of workflow can depend merely on the preference of the user of the device, or perhaps the anatomy of the subject under treatment, type of tissue, and the like. The following table provides example workflows that may be used, each of which providing it's own embodiment of how a method of using the ablation device may be performed.

| | Workflows | | | | |
|---|---|---|---|---|---|
| Steps | A | B | C | D | E |
| 1 | Insert Guide Needles | Insert Guide Needles | Insert Guide Needles | Insert Guide Needles | Insert center needle |
| 2 | Screw in outer coil | Screw in outer coil | Screw in inner coil | Screw in outer coil | Screw in inner coil |
| 3 | Screw in inner coil | Insert center needle | Screw in outer coil | screw in threaded needle | Insert Guide Needles |

-continued

| | | | | | |
|---|---|---|---|---|---|
| 4 | Ablate | Screw in inner coil | Ablate | Ablate | Screw in outer coil |
| 5 | | Ablate | | | Ablate |

| | Workflows | | | |
|---|---|---|---|---|
| Steps | F | G | H | I |
| 1 | Insert Guide Needles | Insert center needle | Insert center needle | Insert Guide Needles |
| 2 | Screw in outer coil | Insert Guide Needles | Insert Guide Needles | Screw in double coil |
| 3 | Insert Center Needle | Screw in inner coil | Screw in outer coil | ablate |
| 4 | Ablate | Screw in outer coil | Screw in Inner coil | |
| 5 | | Ablate | Ablate | |

For each workflow embodiment, the guide needles can optionally be removed prior to ablation. Moreover, for each workflow embodiment, one or more of the components in the tissue from the first ablation can be left in place, while new components can be placed at the next pattern on the template. Regardless, the skilled artisan will appreciate, for example, not only a system that uses guide needles to hold the target tissue, but expanding the use of that system to include a multi-pattern guide template, the combination of which will result in less gaps between the single ablations in the multi-pattern ablations, facilitating the overall desired ablation target of tumor and margin.

In some embodiments, two coils can be placed adjacent to each other on the adjacent hub patterns, and ablation can be conducted between the 2 coils. In some embodiments, after an ablation, each of the coils can be unscrewed to back away from the last ablation for ablating a more shallow tissue. In some embodiments, after one coil is backed out, the other coil, the guide needles, or center straight needle can follow. Alternatively, the straight needles, whether guide needle or center needle, can also be backed out first and then the coils follow. Each handle, for example, can also have a distance marker to show the extent of the change in axial position of a component, such as a coil or needle, relative to another component as a point of reference.

As noted, the hub can have multiple ablation templates to vary the size and shape of the ablation. This size and shape can be varied in the X, Y, and Z directions. Since the ablation can be done multiple times in multiple positions on the hub to vary the size and shape of the ablation in the X, Y, and Z directions, a point of reference can be fixed by leaving a component in place at a previous ablation site. This allows the user of the ablation device to precisely locate a region for the next ablation.

In some embodiments, the target tissue becomes larger at distances that are deeper in the tissue. In these embodiments, for example, if the first ablation is perhaps 15 mm in length, axially, as shown by the length of non-insulated or conductive portion of the electrode tips, the user of the ablation device can back a coil out about 10 mm to ablate another zone, but limit to a more shallow ablation for total ablation length of about 25 mm but leave an overlap of 5 mm. In some embodiments, the first ablation can be more shallow, and the coils can be screwed-in to ablate the next site deeper.

In some embodiments, the target tissue becomes smaller at distances that are deeper in the tissue. In these embodiments, for example, the outer coil can be removed after a first ablation while the inner coil is backed out to the next adjacent more shallow region of tissue to ablate. The inner coil can ablate with a center needle for a smaller diameter ablation, for example.

In some embodiments, the target tissue veers laterally. In these embodiments, instead of a center needle as the second electrode to the smaller coil, adjacent coils can be positioned at different depths, for example, a coil can placed adjacent to the next pattern on the template. The adjacent coils can vary in depth to sculpt the desired ablation pattern. One of skill will appreciate the flexibility of the ablation device at configuring electrodes for sculpting the desired ablation pattern to fit the three dimensional shape and size of the target tissue such as a tumor.

It should be appreciated that there can also be preferences as to how the guide needles are introduced in the workflow. An incremental penetration approach can be used, for example. In some embodiments, the guide needles are inserted a first partial distance, and then the outer and/or inner coil electrodes are inserted at about the same depth; the guide needles are then advanced an additional partial distance, $n_i$, where 'i' is any integer that represents a single step in the incremental penetration of the tissue, and the outer and/or inner coil electrodes are again advanced to about the same depth as the guide needles. The process is repeated until a desired depth is obtained in the target tissue. We found that this technique has the benefit of reducing the splay or inward deviation of the guide needles, seemingly by helping the guide needles stay parallel, which is preferred. The guide needles can remain in place or be removed, depending on the user preference, and the system and/or method that is being used. In some embodiments, it is felt that this stepwise introduction of the components will allow for greater control in the introduction of the components into the target tissue, allowing for even greater accuracy and precision. In some embodiments, 'i' can range from 1 to 10, from 1 to 20, from 1 to 30, from 1 to 40, from 1 to 50, from 1 to 100, from 1 to 500, from 1 to 1000, or any amount or range therein in increments of 1. In some embodiments, each $n_i$ can be selected in a range from 0.1 mm to 50 mm, from 0.1 mm to 40 mm, from 0.1 mm to 30 mm, from 0.1 mm to 20 mm, from 0.1 mm to 10 mm, from 0.1 mm to 5 mm, or any amount or range therein in increments of 0.1 mm. In some embodiments, each $n_i$ can be selected to be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, or any amount or range therein in increments of 0.1 mm. It should be appreciated that each $n_i$ can be the same, or can be independently selected such that any one or any combination of partial distances can be custom-tailored, designed as an approach into a target tissue for an enhanced or optimized, efficiency, accuracy, and/or precision. Likewise, it should be appreciated that not all target tissues are the same, so that the custom-tailored approach can be specific to a particular target tissue type and/or morphology.

The guide needles, inner helical coil, and outer helical coil can each be inserted at a desired, yet continuous rate, and the desired rate can be the same during penetration, regardless of the depth of penetration in the tissue at any point in time; or, the desired rate can vary according to depth. Likewise, the desired rate can vary according to whether it is a rate set for a guide needle, an inner helical coil, or an outer helical coil. In some embodiments, for example, the guide needles and the inner coil and outer coil can each be inserted at the same or similar rate, but at least substantially concurrently, such that each of the tips of the guide needles are at least as deep as the tip of the outer coil and/or inner coil at any given point in time during insertion of the guide needles, inner coil, and outer coil. It is to be appreciated that the tips of the guide needles always need to be at or beyond the tips of the inner coil and/or outer coil to serve as a physical "rail" or "guide" as the inner coil and/or outer coil penetrate the tissue. The rate of penetration of the guide needles, the inner helical coil, and the outer helical coil, ri, where 'i' is any integer that represents a single desired rate in the continuous penetration of the tissue, and the outer and/or inner coil electrodes are advanced at least substantially concurrently with the guide needles. The process is continued until the desired depth is obtained in the target tissue.

In some embodiments, 'i' can range from 1 to 10, from 1 to 20, from 1 to 30, from 1 to 40, from 1 to 50, from 1 to 100, from 1 to 500, from 1 to 1000, or any amount or range therein in increments of 1. In some embodiments, each $r_i$ can be selected in a range from 0.1 mm/second to 50 mm/second, from 0.1 mm/second to 40 mm/second, from 0.1 mm/second to 30 mm/second, from 0.1 mm/second to 20 mm/second, from 0.1 mm/second to 10 mm/second, from 0.1 mm/second to 5 mm/second, or any amount or range therein in increments of 0.1 mm/second. In some embodiments, each $n_i$ can be selected to be 1 mm/second, 2 mm/second, 3 mm/second, 4 mm/second, 5 mm/second, 6 mm/second, 7 mm/second, 8 mm/second, 9 mm/second, 10 mm/second, 11 mm/second, 12 mm/second, 13 mm/second, 14 mm/second, 15 mm/second, 16 mm/second, 17 mm/second, 18 mm/second, 19 mm/second, 20 mm/second, 21 mm/second, 22 mm/second, 23 mm/second, 24 mm/second, 25 mm/second, 26 mm/second, 27 mm/second, 28 mm/second, 29 mm/second, 30 mm/second, 31 mm/second, 32 mm/second, 33 mm/second, 34 mm/second, 35 mm/second, 36 mm/second, 37 mm/second, 38 mm/second, 39 mm/second, 40 mm/second, 41 mm/second, 42 mm/second, 43 mm/second, 44 mm/second, 45 mm/second, 46 mm/second, 47 mm/second, 48 mm/second, 49 mm/second, 50 mm/second, or any amount or range therein in increments of 0.1 mm/second. It should be appreciated that each $r_i$ can be the same, or can be independently selected such that any one or any combination of rates can be custom-tailored, designed as an approach into a target tissue for an enhanced or optimized, efficiency, accuracy, and/or precision. Likewise, it should be appreciated that not all target tissues are the same, so that the custom-tailored approach can be specific to a particular target tissue type and/or morphology.

We claim:

1. A guided, dual coil ablation system with impedance feedback, the system comprising:
   an outer coil electrode having an inner diameter ranging from 4 mm to 40 mm, a lumen having a luminal surface forming the inner diameter, an outer length, and an outer coil axis; the outer coil electrode configured as an impedance electrode;
   an inner coil electrode having an outer diameter that ranges from 2 mm to 39 mm and is 1.0 mm to 38.0 mm smaller than the inner diameter of the outer coil electrode, an outer surface, an inner length, and an inner coil axis;
   a plurality of guide needles including
      a first guide needle having a first guide axis and a first guide length; and,
      a second guide needle having a second guide axis and a second guide length; and,
   a hub having a first ablation template, the first ablation template including a first outer electrode port adapted for receiving the outer coil electrode, a first inner electrode port adapted for receiving the inner coil electrode, a first guide port for receiving the first guide needle, and a second guide port for receiving the second guide needle; wherein, the first ablation template is configured for
      positioning the first guide needle relative to the second guide needle in or around a tissue to be ablated such that the first and second guide needles are positioned between the inner and outer coil electrodes, the positioning including using the first guide port and the second guide port to align the first guide axis with the second guide axis in an at least substantially parallel arrangement; and,
      the inner coil electrode and the outer coil electrode are configured for creating an annular ablation region around the first guide needle and the second guide needle in the tissue to be ablated upon assembly of the system, the inner coil electrode aligned at least substantially concentric with the outer coil electrode; the annular ablation region configured to be (i) bordered by the outer surface of the inner coil electrode and the luminal surface of the outer coil electrode and (ii) having a thickness ranging from 0.5 mm to 10 mm;
   wherein, the plurality of guide needles secure the tissue while guiding placement of the outer coil electrode and the inner coil electrode for the ablation.

2. The ablation system of claim 1, wherein
   the plurality of guide needles further includes a third guide needle having a third guide axis and a third guide length;
   the annular ablation region is also around the third guide needle with the third guide axis in an at least substantially parallel arrangement with the first guide axis and with the second guide axis; and,
   the first ablation template further includes a third guide port for receiving the third guide needle;
   wherein, the plurality of guide needles are configured to include an impedance electrode to monitor the position of the electrode as it is advanced into a tissue of a subject.

3. The ablation system of claim 2, wherein each needle in the plurality of guide needles is configured as an impedance electrode to monitor the position of each needle as it is advanced into the tissue of the subject.

4. The ablation device of claim 1, wherein,
   the outer coil electrode has an outer pitch;
   the inner coil electrode has an inner pitch; and,
   the outer pitch is positioned to have a phase-offset with respect to the inner pitch, the phase-offset ranging from between 30° to 180°.

5. The ablation system of claim 1, further comprising:
   an outer coil electrode handle in an operable connection with the outer coil electrode and configured for adjusting the depth of the outer coil electrode in the tissue; and,
   an inner coil electrode handle in an operable connection with the inner coil electrode and configured for adjusting the depth of the inner coil electrode in the tissue.

6. The ablation system of claim 1, wherein the inner coil includes
a straight shaft; and,
a spiral protrusion wrapping around the straight shaft.

7. The ablation system of claim 1, wherein the hub is a multi-pattern guide template further comprising 1-10 additional ablation templates, each of the 1-10 additional ablation templates comprising a respective outer electrode port, inner electrode port, and a pair of guide ports, and the 1-10 additional ablation templates can be used to create a plurality of ablation patterns to ablate the tissue.

8. The ablation system of claim 1, wherein the outer electrode is operable to provide a feedback response for monitoring the electrical impedance of a tissue as the outer electrode penetrates the tissue of the subject to indicate the position of the outer electrode in the tissue of the subject.

9. A method of ablating tissue, the method comprising:
obtaining an ablation system having an inner coil electrode with an outer surface and an inner pitch, an outer coil electrode with an inner surface and an outer pitch, a first guide needle with a first guide axis, a second guide needle with a second guide axis; and, a hub having a first ablation template with a first outer electrode port adapted for receiving the outer coil electrode, a first inner electrode port adapted for receiving the inner coil electrode, a first guide port for receiving the first guide needle, and a second guide port for receiving the second guide needle; wherein, the outer electrode is configured as an impedance electrode;
locating a tissue for ablation;
aligning the first ablation template over the tissue;
receiving the first guide needle in the first guide port of the first ablation template;
inserting the first guide needle into the tissue;
receiving the second guide needle in the second guide port of the first ablation template;
inserting the second guide needle into the tissue;
creating an annular ablation region in the tissue to be ablated, the creating including
receiving the inner coil electrode in the first inner electrode port of the first ablation template;
receiving the outer coil electrode in the first outer electrode port of the first ablation template;
inserting the outer coil electrode into the tissue, the inserting including slidably translating the luminal surface of the outer coil electrode around the first guide needle and the second guide needle, wherein the outer coil electrode surrounds the first guide needle and the second guide needle; the inserting including navigating the penetration of the outer electrode into the tissue, the navigating including monitoring the electrical impedance of the tissue with the position of the outer coil electrode;
inserting the inner coil electrode into the tissue, the inserting including slidably translating the outer surface of the inner coil electrode concentric with the outer coil electrode to create the annular ablation region; wherein, the first guide needle and the second guide needle are in the annular ablation region,
securing the tissue and guiding the dual coil ablation system into the tissue for the ablation, the securing and the guiding facilitated by the first guide needle and the second guide needle, removing the first guide needle and the second guide needle from the tissue, and, ablating the tissue by delivering energy through the inner and outer coils.

10. The method of claim 9, wherein the ablation system further includes a third guide needle having a third guide axis; and, the first ablation template further includes a third guide port for receiving the third guide needle; wherein each of the first guide needle, second guide needle, and third guide needle is configured as an impedance electrode to monitor the position of each needle as it is advanced into the tissue of the subject, the method further comprising
inserting the third guide needle into the tissue;
receiving the third guide needle in the third guide port of the first ablation template; and,
avoiding tissue structures in the subject that are not intended to be ablated; the avoiding including
navigating the position of the first guide needle, the second guide needle, and the third guide needle in the tissue to be ablated; and,
navigating the outer coil electrode in the tissue to be ablated;
the navigating including monitoring the electrical impedance of the first guide needle, the second guide needle, and the third guide needle to monitor the position of each needle as it is advanced into the subject to fix the position of the tissue to be ablated with the guide needles, and guide the outer coil electrode into the tissue to be ablated with the guide needles;
wherein,
the inserting of the outer coil electrode into the tissue includes slidably translating the luminal surface of the outer coil electrode over the first guide needle, the second guide needle, and the third guide needle;
the first guide needle, the second guide needle, and the third guide needle are in the annular ablation region; and,
the removing includes removing the first guide needle, the second guide needle, and the third guide needle from the tissue.

11. The method of claim 10,
wherein, the navigating further includes monitoring the electrical impedance of the outer coil electrode as it is advanced into the subject to monitor the position of the outer coil electrode relative to the tissue to be ablated for the avoiding of the tissue not intended to be ablated.

12. The method of claim 10, wherein the tissue structures that are not intended to be ablated are selected from the group consisting of nerve tissue, urethra, bowel, and prostate capsule.

13. The method of claim 10, further comprising:
navigating the ablation process to a completion, the navigating including monitoring the extent of ablation through the one or more impedance electrodes during ablation in the annular ablation region.

14. The method of claim 9, further comprising
establishing a phase-offset between the outer pitch of the outer coil electrode and the inner pitch of the inner coil electrode, the phase-offset ranging from between 30° to 180°; and,
ablating the tissue within the annular ablation region formed having the phase offset between the outer coil electrode and the inner coil electrode.

15. The method of claim 9, further comprising:
adjusting a depth of the outer coil electrode with an outer coil electrode handle in an operable connection with the outer coil electrode; and,
adjusting a depth of the inner coil electrode with an inner coil electrode handle in an operable connection with the inner coil electrode.

16. The method of claim 9, wherein the hub is a multi-pattern guide template further comprises 1 to 10 additional templates, each of the 1-10 additional ablation templates comprising a respective outer electrode port, inner electrode port, and pair of guide ports, and the method further comprises
creating an ablation pattern to ablate the tissue with a plurality of the 1-10 additional ablation templates; and, ablating the tissue with the ablation pattern.

17. A method of ablating a prostate tissue of a subject, comprising:
obtaining an ablation device having
an outer coil electrode having an inner diameter ranging from 4 mm to 40 mm, a lumen having a luminal surface forming the inner diameter, an outer length, and an outer coil axis; wherein, the outer electrode is configured as an impedance electrode;
an inner coil electrode having an outer diameter that ranges from 2 mm to 39 mm and is 1.0 mm to 38.0 mm smaller than the inner diameter of the outer coil electrode, an outer surface, an inner length, and an inner coil axis;
a plurality of guide needles including
a first guide needle having a first guide axis and a first guide length; and,
a second guide needle having a second guide axis and a second guide length;
and,
a hub having a first ablation template, the first ablation template including a first outer electrode port adapted for receiving the outer coil electrode, a first inner electrode port adapted for receiving the inner coil electrode, a first guide port for receiving the first guide needle, and a second guide port for receiving the second guide needle;
locating the prostate tissue for ablation;
aligning the first ablation template over the prostate tissue;
receiving the first guide needle in the first guide port of the first ablation template;
inserting the first guide needle into the prostate tissue;
receiving the second guide needle in the second guide port of the first ablation template;
inserting the second guide needle into the prostate tissue;
creating an annular ablation region in the prostate tissue, the creating including
receiving the inner coil electrode in the first inner electrode port of the first ablation template, and receiving the outer coil electrode in the first outer electrode port of the first ablation template;
inserting the outer coil electrode into the prostate tissue, the inserting including slidably translating the luminal surface of the outer coil electrode around the first guide needle and the second guide needle, wherein the outer coil electrode contains the first guide needle and the second guide needle; wherein the inserting includes monitoring the electrical impedance of the outer coil electrode as it is advanced into the subject to position of the outer coil electrode in the prostate tissue while avoiding any tissue not intended to be ablated;
inserting the inner coil electrode into the prostate tissue, the inserting including slidably translating the outer surface of the inner coil electrode concentric with the outer coil electrode to create the annular ablation region; wherein, the first guide needle and the second guide needle are in the annular ablation region, securing the tissue and guiding the dual coil ablation system into the tissue for the ablation, the securing and the guiding facilitated by the first guide needle and the second guide needle, removing the first guide needle and the second guide needle from the tissue, and, ablating the tissue by delivering energy through the inner and outer coils.

18. The method of claim 17, wherein the ablation system further includes a third guide needle having a third guide axis; and, the first ablation template further includes a third guide port for receiving the third guide needle; wherein each of the first guide needle, second guide needle, and third guide needle is configured as an impedance electrode to monitor the position of each needle as it is advanced into the tissue of the subject, and the method further comprising
inserting the third guide needle into the tissue;
receiving the third guide needle in the third guide port of the first ablation template; and,
avoiding tissue structures in the subject that are not intended to be ablated; the avoiding including
navigating the position of the first guide needle, the second guide needle, and the third guide needle in the tissue to be ablated; and,
navigating the outer coil electrode in the tissue to be ablated;
the navigating including monitoring the electrical impedance of the first guide needle, the second guide needle, and the third guide needle to monitor the position of each needle as it is advanced into the subject to fix the position of the tissue to be ablated with the guide needles, and guide the outer coil electrode into the tissue to be ablated with the guide needles;
wherein,
the inserting of the outer coil electrode into the tissue includes slidably translating the luminal surface of the outer coil electrode over the first guide needle, the second guide needle, and the third guide needle;
the first guide needle, the second guide needle, and the third guide needle are in the annular ablation region; and,
the removing includes removing the first guide needle, the second guide needle, and the third guide needle from the prostate tissue.

19. The method of claim 17, further comprising
establishing a phase-offset between the outer pitch of the outer coil electrode and the inner pitch of the inner coil electrode, the phase-offset ranging from between 30° to 180°; and,
ablating the tissue within the annular ablation region formed having the phase offset between the outer coil electrode and the inner coil electrode.

20. The method of claim 17, the ablation system further comprising one or more impedance electrodes operable to provide a feedback response for monitoring the electrical impedance of any tissue in contact with the one or more impedance electrodes, and the method further comprising navigating the first guide needle and/or second guide needle, the inner coil electrode and/or the outer coil electrode, and the extent of ablation, wherein the navigating includes:
monitoring the position of the first guide needle or the second guide needle in the any tissue in contact with the first guide needle and/or the second guide needle;
monitoring the position of the inner coil electrode or the outer coil electrode in the any tissue in contact with the inner coil electrode or the outer coil electrode; or, monitoring the extent of ablation of the prostate tissue through the one or more impedance electrodes during ablation.

\* \* \* \* \*